(12) United States Patent
Nidorf

(10) Patent No.: US 11,944,594 B2
(45) Date of Patent: *Apr. 2, 2024

(54) TREATMENT OR PREVENTION OF CARDIOVASCULAR EVENTS VIA THE ADMINISTRATION OF A COLCHICINE DERIVATIVE

(71) Applicant: MURRAY AND POOLE ENTERPRISES LTD, Gibraltar (GI)

(72) Inventor: Mark Nidorf, Menora (AU)

(73) Assignee: MURRAY AND POOLE ENTERPRISES LTD, Gibraltar (GI)

(*) Notice: Subject to any disclaimer, the term of this patent is extended or adjusted under 35 U.S.C. 154(b) by 0 days.

This patent is subject to a terminal disclaimer.

(21) Appl. No.: 18/144,470

(22) Filed: May 8, 2023

(65) Prior Publication Data

US 2023/0270697 A1 Aug. 31, 2023

Related U.S. Application Data

(63) Continuation of application No. 16/952,617, filed on Nov. 19, 2020, now Pat. No. 11,666,545, which is a continuation of application No. 16/390,606, filed on Apr. 22, 2019, now Pat. No. 10,842,761, which is a continuation of application No. 14/440,147, filed as application No. PCT/AU2013/001261 on Nov. 1, 2013, now Pat. No. 10,265,281.

(30) Foreign Application Priority Data

Nov. 2, 2012 (AU) ................................. 2012904828
Nov. 5, 2012 (AU) ................................. 2012904868

(51) Int. Cl.
| | |
|---|---|
| *A61K 31/165* | (2006.01) |
| *A61K 31/37* | (2006.01) |
| *A61K 31/4365* | (2006.01) |
| *A61K 31/616* | (2006.01) |
| *A61K 45/06* | (2006.01) |

(52) U.S. Cl.
CPC ............ *A61K 31/165* (2013.01); *A61K 31/37* (2013.01); *A61K 31/4365* (2013.01); *A61K 31/616* (2013.01); *A61K 45/06* (2013.01)

(58) Field of Classification Search
CPC .... A61K 31/165; A61K 45/06; A61K 31/616; A61K 31/37; A61K 31/4365
See application file for complete search history.

(56) References Cited

U.S. PATENT DOCUMENTS

| | | |
|---|---|---|
| 3,173,876 A | 3/1965 | Zobrist |
| 3,276,586 A | 10/1966 | Rosaen |
| 3,541,005 A | 11/1970 | Strathmann et al. |
| 3,541,006 A | 11/1970 | Bixler et al. |
| 3,546,142 A | 12/1970 | Michaels et al. |
| 4,285,987 A | 8/1981 | Ayer et al. |
| 8,415,395 B1 | 4/2013 | Davis et al. |
| 2002/0015735 A1 | 2/2002 | Hedden |
| 2002/0169145 A1 | 11/2002 | Shah et al. |
| 2006/0171948 A1 | 8/2006 | Weinstein et al. |
| 2006/0286108 A1 | 12/2006 | Bell |
| 2007/0281906 A1 | 12/2007 | Dalton et al. |
| 2008/0039408 A1 | 2/2008 | Freudenberger |
| 2009/0093548 A1 | 4/2009 | Davis et al. |
| 2009/0170952 A1 | 7/2009 | Davis et al. |
| 2009/0191564 A1 | 7/2009 | Francis et al. |
| 2009/0299155 A1 | 12/2009 | Yang |
| 2009/0304769 A1 | 12/2009 | Kunkel et al. |
| 2009/0312430 A1 | 12/2009 | Sun et al. |
| 2011/0046227 A1 | 2/2011 | Davis |
| 2011/0046228 A1 | 2/2011 | Davis |
| 2011/0190397 A1 | 8/2011 | Davis |

(Continued)

FOREIGN PATENT DOCUMENTS

| | | |
|---|---|---|
| CN | 1939290 A | 4/2007 |
| CN | 101485637 A | 7/2009 |

(Continued)

OTHER PUBLICATIONS

Liu et al. European review for medical and Pharmacological sSciences 2014; 18:2918; 2926.*
Hossain et al. (Diabetes, Metabolic Syndrome and Obesity: Targets and Therapy 2014:7 587-591).*
Al-Goblan (Diabetes Metab Syndr. Obes (2014); 7; 587-591).*
Extended European Search Report dated Feb. 9, 2022, European Application No. 21185610.9, pp. 1-15.
Massimo Imazio, "Colchicine for Pericarditis," Trends in Cardiovascular Medicine, vol. 25, Issue 2, Feb. 2015, pp. 129-136 (Abstract Provided).

(Continued)

*Primary Examiner* — Shirley V Gembeh
(74) *Attorney, Agent, or Firm* — BioPharma Law Group, PLLC

(57) ABSTRACT

A method for reducing a risk of at least one cardiovascular event in a subject in need thereof, which includes administering, orally once per day to the subject, a composition comprising about 0.5 total mg of (i) colchicine, (ii) a pharmaceutically acceptable salt of (i), or any combination of (i) and (ii), wherein the at least one cardiovascular event is chosen from myocardial infarction (MI), stroke, coronary revascularization, unstable angina requiring hospitalization, cardiac arrest, and cardiovascular death; wherein the subject has no contra-indications to colchicine therapy, and has at least one risk factor; and vii. therapy with at least one drug chosen from aspirin, clopidogrel, statins, beta blockers, calcium blockers, and ACE inhibitors; and wherein the composition reduces the risk of the subject experiencing the at least one cardiovascular event by a greater percentage than a composition that does not include colchicine or the pharmaceutically acceptable salt thereof.

24 Claims, 4 Drawing Sheets

(56) References Cited

U.S. PATENT DOCUMENTS

| | | |
|---|---|---|
| 2011/0207826 A1 | 8/2011 | Schwarz et al. |
| 2015/0094322 A1 | 4/2015 | Riel |
| 2015/0094323 A1 | 4/2015 | Riel |

FOREIGN PATENT DOCUMENTS

| | | |
|---|---|---|
| CN | 101485638 A | 7/2009 |
| CN | 101536990 | 9/2009 |
| CN | 101732274 A | 6/2010 |
| EA | 008224 B1 | 4/2007 |
| JP | 2000034224 A | 2/2000 |
| JP | 2005523885 A | 8/2005 |
| JP | 2011140498 A | 7/2011 |
| JP | 2012519725 A | 8/2012 |
| JP | 2012236846 A | 12/2012 |
| JP | 2013510873 A | 3/2013 |
| WO | 1992015282 A2 | 9/1992 |
| WO | 2002/072034 A2 | 9/2002 |
| WO | 2003053219 | 7/2003 |
| WO | 2006/039022 A2 | 4/2006 |
| WO | 2007048004 A2 | 4/2007 |
| WO | 2008131192 A2 | 10/2008 |
| WO | 2010046628 A1 | 4/2010 |
| WO | 2010103365 | 9/2010 |
| WO | 2011060256 | 5/2011 |
| WO | 2012100949 | 8/2012 |
| WO | 2013155478 | 10/2013 |
| WO | 2014066944 | 5/2014 |
| WO | 2014/170755 A2 | 10/2014 |

OTHER PUBLICATIONS

S. Robertson et al., "Colchicine markedly suppresses trans-coronary and cellular release of inflammasome-derived cytokines in Acute Coronary Syndrome (ACS) patients," Heart and Lung Circulation, vol. 24, Supplement 3, Jan. 2015, S115 (Abstract Provided).
Extended European Search Report dated Apr. 13, 2022, European Application No. 21191811.5, pp. 1-15.
Peter Libby et al., "Inflammation in Atherosclerosis: Transition from Theory to Practice," Circulation Journal, vol. 74, Feb. 2010, pp. 213-220.
W Zhang et al., "EULAR evidence based recommendations for gout. Part II: Management. Report of a task force of the EULAR Standing Committee For International Clinical Studies Including Therapeutics (ESCISIT)," Annals of the rheumatic diseases 65.10 (2006): 1312-1324.
WA Today, "Gout Medicine Found to Halve Heart Attack Risk," Nov. 6, 2012, Retrieved from the Internet: https://www.watoday.com.au/national/western-australia/gout-medicine-found-to-halve-heart-attack-risk-20121106-28v5e.html, pp. 1-2.
Communication of Notice of Opposition dated Apr. 25, 2022, European Application No. 13851803.0, pp. 1-39.
P. M. Ridker et al., "Antiinflammatory Therapy with Canakinumab for Atherosclerotic Disease," The New England Journal of Medicine, vol. 377, No. 12, Sep. 2017, pp. 1119-1131.
Kaivan Vaidya et al., "Colchicine Therapy and Plaque Stabilization in Patients with Acute Coronary Syndrome: a CT coronary angiography study." JACC: Cardiovascular Imaging, vol. 11, No. 2, 2018, pp. 305-316.
ARTG Search (AU Government), Retrieved from the Internet: www.tga.gov.au, pp. 1-2.
Therapeutic Goods Administration (TGA), "Australian Product Information Lengout (Colchicine) Tablets," Retrieved from the Internet: https://www.ebs.tga.gov.au/ebs/picmi/picmirepository.nsf/PICMI?OpenForm&t=pi&q=Lengout, Aug. 28, 2020, pp. 1-13.
Parvez Hossain et al., "Obesity and Diabetics in the Develpoing World - A Growing Challenge," New England Journal of Medicine; 356:213-215, Jan. 2007, pp. 1-6.
Abdullah S. Al-Goblan et al., "Mechanism linking diabetes mellitus and obesity," Diabetes, Metabolic Syndrome and Obesity: Targets and Therapy, (2014): 587-591.

Adler et al., "Colchicine treatment for recurrent pericarditis: a decade of experience," Circulation, 97:2183-2185, 1998.
Antonopoulis et al., "Statins as Anti-inflammatory agents in Atherogenesis: Molecular mechanisms and lessons from the recent clinical trials," Curr. Pharma. Design, 18:1519-1530, 2012.
Crittenden, D., et al., "Colchicine Use Is Associated with decreased prevalence of Myocardial Infarction in Patients with Gout," J. Rheumatol., 39:1458-1464, 2012.
Finkelstein et al., "Colchicine for the prevention of Postpericardiotomy Syndrome," Herz, 27(8):791-794, 2002.
Gabrielyan, R.S., et al. "Comparative effects of losartan and losartan colchicines combination therapy in unstable angina patients with hyperuricaemia," Eur .J. Echocard., 7:S83, 2006.
Hufford, C.D., et al., "(13)C- and (1)H-NMR. Assignments for Colchicine Derivatives," Helvetica Chimica Acta, 63(1):50-56, 1980.
Mazio et al., "Colchicine as first-Choice therapy for recurrent pericarditis," Arch. Intern Med., 165(17):1987-1991, 2005.
Imazio et al., "Colchicine for recurrent pericarditis (CORP): a randomized trial," Ann. Intern. Med., 155(7):409-414, 2011.
Imazio et al., "Colchicine for the Prevention of the Post-pericardiotomy Syndrome (COPPS): a multicenter, randomized, double-blind, placebo-controlled trial," Eur. Heart J., 31:2749-2754, 2010.
Imazio et al., "Colchicine in addition to conventional therapy for acute pericarditis," Circulation, 112(13):2012-2016, 2005.
Imazio et al., "Colchicine prevents early postoperative pericardial and pleural effusions," Am. Heart J., 162(3):527-532, 2011.
International Preliminary report on Patentability for PCT/AU2013/001261 dated May 5, 2015. pp. 1-6.
Judkins, C., et al., "LoDoCo: Low Dose Colchicine in stable coronary artery disease and the effect on hs-CRP and brachial flow mediated dilation," CSANZ Abstracts, pp. S36, Abstract No. 89, 2011.
Kouroupis, P., et al., "From Colchicine and some of its derivatives to 1,2,3,9, 10-Pentamethoxybenzo[alpha] heptalenes," Helv. Chimica Acta, 78:1247-1277, 1995.
Lagrue, G., et al., "Effect of colchicine on atherosclerosis—I. Clinical and biological studies" Clin. Physiol. Biochem. 3(5):221-222, 1985.
Lee et al., "Pharmacokinetic comparison of sustained- and immediate-release oral formulations of cilostazol in healthy Korean subjects: a randomized, open-label, 3-part, sequential, 2-period, crossover, single-dose, food-effect, and multiple-dose study," Clin. Ther., 33(12):2038-53, 2011.
Maisch et al., "Guidelines on the Diagnosis and Management of Pericardial Diseases," Eur. Heart J., 25(7):587-610, 2004.
Malone et al., "Pharmacokinetic evaluation of a new oral sustained release dosage form of tramadol," Brit. J. Pharmacol., 57(3):270-278, 2003.
Marcher, U., "Co-Processed Lactose-based excipients for Direct Compression," Meggle, Excipients & Technology, pp. 1-52, 2012.
Marcher, U., "Retalac, a new excipient for direct compression of sustained release formulations," http://www.pharmtech.com/meggle, Meggle, 1 page, Jul. 9, 2010.
Nakamura, Y., et al., "Role of microtubules in ischemic preconditioning against myocardial infarction," Cardiovas. Res., 64:322-330, 2004.
Nidorf et al., "Low-dose colchicine for secondary prevention of cardiovascular disease," (The LoDoCo Trial) ACTR No. ACTR12610000293066, ethics approval at QII Jul. 2008.
Nidorf, S., et al., "Low-Dose Colchicine for secondary prevention of cariovascular disease," J. Am. Coll. Cardiol., 61:404-410, pp. 1-4, 2013.
O'Keefe Jr., J., et al., "Ineffectiveness of Colchicine for the prevention of Restenosis after coronary angioplasty," J. Am. Coll. Cardiol., 19:1597-1600, 1992.
Raju, N., et al., "Effect of colchicine compared with placebo on high sensitivity C-reactive protein in patients with 25 acute coronary syndrome or acute stroke: a pilot randomized controlled trial",: J. Thrombosis and Thrombolysis, 33:88-94, 2011.

(56) References Cited

OTHER PUBLICATIONS

Schlesinger, N., et al., "Canakinumab reduces the risk of acute gouty arthritis flares during initiation of allopurinol treatment: Results of a double-blind, randomized study", Animals Rheum. Dis. 70:1264-1271, 2011.
Seferovic, P., et al., "Management Strategies in Pericardial Emergencies", Herz, 31:891-900, 2006.
Sparano, D.M. and R. Parker Ward, "Pericarditis and Pericardial Effusion: Management Update", Cardiovas. Med., 13:543-555, 2011.
Written Opinion and International Search Report for PCT Application No. PCT/IB2014/001201 mailed Nov. 13, 2014, pp. 1-7.
Written Opinion and Search Report for PCT/AU2013/001261 dated Dec. 16, 2013, pp. 1-5.
Imazio et al., "Colchicine reduces postoperative atrial fibrillation: results of the Colchicine for the Prevention of the Postpericardiotomy Syndrome (COPPS) atrial fibrillation substudy," Circulation, 124(21):2290-2295, 2011.
Nidorf et al., "Effect of Colchicine (0.5 mg Twice Daily) on High-Sensitivity C-Reactive Protein Independent of Aspirin and Atorvastatin in Patients with Stable Coronary Artery Disease," Am. J. Cardio., 99:805-807 2007.
Siepmann et al., "Predicting drug release from HPMC/lactose tablets," Int. J. Pharmaceutics, 441:826-834, 2013.
Zema et al., Different HPMC viscosity grades as coating agents for an oral time and/or site controlled delivery system: An investigation into the mechanisms governing drug release, J. Pharma. Sciences, 96(6):1527-1536, 2007.
International Preliminary report on Patentability for PCT/IB2014/001201 dated Oct. 20, 2015, pp. 1-8.
W. Hollander et al., "Suppression of atheromatous fibrous plaque-formation by antiproliferative and antiinflammatory drugs", Circulation Research, vol. 34, 1974, pp. 1131-1141. (Abstract submitted).
M. Nidorf et al., "The Effect of Low Dose Colchicine on hs-CRP in Patients with Stable Coronary Artery Disease (CAD) Independent of Aspirin and Statin Therapy", Heart, Lung and Circulation, vol. 16, 2007, p. S70.
Russell Ross, "Atherosclerosis—An Inflammatory Disease", The New England Journal of Medicine, vol. 340, No. 2, Jan. 1999, pp. 115-126.

Ew Chia et al., "Colchicine suppresses neutrophil superoxide production in a murine model of gouty arthritis: a rationale for use of low-dose colchicine", British Journal of Pharmacology (2008) 153, pp. 1288-1295.
Finkelstein et al., "Colchicine poisoning: the dark side of an ancient drug." Clinical Toxicology 48.5 (2010), pp. 407-414 (Abstract submitted).
Lily PH. Yang, "Oral colchicine (Colcrys [R]) in the Treatment and Prophylaxis of Gout" Drugs, Aug. 20, 2010, 70(12), pp. 1603-1613 (Abstract submitted).
Renu Virmani et al., "Lessons From Sudden Coronary Death: A Comprehensive Morphological Classification Scheme for Atherosclerotic Lesions", Arterioscler Thromb Vasc Biol. 2000;20:1262-1275.
Lin-Shong Li et al., "Colchicine in Treatment of Intractable Postpericardiotomy Syndrome in an Elderly Patient", International Journal of Gerontology, vol. 5, No. 2, Jun. 2009, pp. 120-122.
Joseph L. Jorizzo et al., "Behcet's syndrome: Immune regulation, circulating immune complexes, neutrophil migration, and colchicine therapy", Journal of the American Academy of Dermatology, vol. 10, Issue 2, Part 1, Feb. 1984, pp. 205-214 (Abstract submitted).
Kenya Saji et al., "Colchicine, a Microtubule Depolymerizing Agent, Inhibits Myocardial Apoptosis in Rats", Tohoki J. Exp. Med., 2007, vol. 213, pp. 139-148.
Charles W. Denko et al., "Modification of Cholesterol Crystal-Induced Inflammation", Agents and Actions, 1980, vol. 10/4, pp. 353-357.
David Gregg et al., "Platelets and Cardiovascular Disease", Circulation, vol. 108, No. 13, 2003, pp. e88-e90.
ANZCTR, "LoDoCo Study: The effect of low dose colchicine on the natural history of atherosclerosis," Trial Registered on ANZCTR, Trial Registration No. ACTRN12610000293066, Submitted Apr. 8, 2010, pp. 1-5.
ANZCTR, "LoDoCo Trial: The effect of low dose colchicine on the natural history of patients with stable coronary artery disease," Trial Registered on ANZCTR, Trial Registration No. ACTRN12610000293066, Submitted Apr. 8, 2010, pp. 1-5.
ANZCTR, "LoDoCo Trial: The effect of low dose colchicine on the natural history of patients with stable coronary artery disease, " Trial Registered on ANZCTR, Trial Registration No. ACTRN12610000293066, Submitted Apr. 8, 2010, pp. 1-8.
Johan Frostegard, "Immunity, atherosclerosis and cardiovascular disease," BMC medicine 11.1 (2013): 1-13.

\* cited by examiner

TREATMENT OR PREVENTION OF CARDIOVASCULAR EVENTS VIA THE ADMINISTRATION OF A COLCHICINE DERIVATIVE

RELATED APPLICATIONS

This application is a continuation of U.S. patent application Ser. No. 16/952,617, file Nov. 19, 2020, which is a continuation of U.S. patent application Ser. No. 16/390,606, filed Apr. 22, 2019, which is a continuation of U.S. patent application Ser. No. 14/440,147, filed May 1, 2015, which is a National Stage Entry of PCT Application No. PCT/AU2013/001261, filed Nov. 1, 2013, which claims the benefit of AU2012/904868, filed Nov. 5, 2012 and AU2012/904828, filed Nov. 2, 2012, the entire contents of which are incorporated herein by reference.

TECHNICAL FIELD

A method for the treatment and/or prevention of cardiovascular events in patients with established atherosclerotic vascular disease.

BACKGROUND ART

The following discussion of the background art is intended to facilitate an understanding of the present invention only. The discussion is not an acknowledgement or admission that any of the material referred to is or was part of the common general knowledge as at the priority date of the application.

In patients with atherosclerotic vascular disease, the diseased vessel wall is subject to injurious forces that promote plaque build-up and instability that may lead to coronary occlusion resulting in heart attack, ischemic stroke and sudden death.

The response to injury within the diseased vessel is dependent on the architecture and content of atherosclerotic plaques. Lipid-rich plaques with a neo-vascular base are particularly susceptible to the effect of injury, which may leave them vulnerable to neutrophil infiltration. Neutrophils that enter the interstitial space may become activated upon exposure to the plaque contents, inciting an aggressive inflammatory response that may accelerate plaque instability increasing the risk of plaque enlargement and rupture and hence increasing the risk of clinical events.

Despite routine use of anti-platelet and statin therapy, patients with atherosclerotic vascular disease continue to be at risk of cardiovascular events, possibly because these treatments fail to target some of the inflammatory pathways implicated in the disease.

A number of additional treatments exist for the prevention or reduction in risk of coronary heart disease, including: antiplatelet agents (besides aspirin), anticoagulants, angiotensin-converting-enzyme inhibitors (ACEIs); aldosterone receptor antagonists (ARAs); beta-blockers calcium channel blockers and/or nitrates.

However, many of these treatments are recommended for acute conditions and do not address or provide for a long-term reduction in cardiovascular events in patients with clinically stable atherosclerotic vascular disease.

It is against this background that the present invention has been developed.

The present invention seeks to overcome, or at least ameliorate, one or more of the deficiencies of the prior art mentioned above, or to provide the consumer with a useful or commercial choice.

SUMMARY OF INVENTION

The present invention provides a method for the treatment or prevention of a cardiovascular event in a subject comprising the step of:
   administering a therapeutically effective amount of a compound of formula (I), a known colchicine derivative and/or a salt thereof.

The present invention provides a method for the treatment or prevention of a cardiovascular event in a subject with atherosclerotic vascular disease comprising the step of:
   administering a therapeutically effective amount of a compound of formula (I), a known colchicine derivative and/or a salt thereof.

The present invention further provides a method for the treatment or prevention of a cardiovascular event in a subject with atherosclerotic vascular disease comprising the step of:
   administering a therapeutically effective amount of a compound of formula (I), a known colchicine derivative and/or a salt thereof and one or more additional agents selected from the list comprising: a statin and/or an anti-platelet agent.

Preferably the atherosclerotic vascular disease is a coronary disease. The coronary disease may be stable or unstable.

The invention further provides a method for the treatment or prevention of a cardiovascular event in a subject comprising the step of:
   administering a therapeutically effective amount of a compound of formula (I), a known colchicine derivative and/or a salt thereof
wherein the subject has coronary disease prior to administration of the therapeutically effective amount of a compound of formula (I), a known colchicine derivative and/or a salt thereof. Preferably the coronary disease is a stable coronary disease.

The present invention provides a method for reducing or preventing cholesterol crystal induced inflammation within atherosclerotic plaques in a subject, comprising the step of
   administering a dosage of 0.5 mg or 0.6 mg of a compound of formula (I), a known colchicine derivative and/or a salt thereof.

The invention also provides for the use of a compound of formula (I), a known colchicine derivative and/or a salt thereof in the preparation of a medicament for the treatment or prevention of a cardiovascular event.

In addition, the invention provides a composition for the prevention or treatment of a cardiovascular event in a subject, the composition comprising a therapeutically effective amount of a compound of formula (I), a known colchicine derivative and/or a salt thereof and one or more pharmaceutically acceptable additives, excipients carriers and/or diluents.

Preferably, the composition comprises 0.5 mg or 0.6 mg of a compound of formula (I), a known colchicine derivative and/or a salt thereof.

Preferably, the composition further comprises one or more additional agents selected from the list comprising: a statin and/or an anti-platelet agent.

The present invention provides a regimen for the treatment or prevention of a cardiovascular event in a subject, the regimen comprising the step of:
   administering a dosage of 0.5 mg or 0.6 mg of a compound of formula (I), a known colchicine derivative and/or a salt thereof once per day.

The present invention also provides a regimen for reducing or preventing cholesterol crystal induced inflammation within atherosclerotic plaques in a subject, the regimen comprising the step of:
   administering a dosage of 0.5 mg or 0.6 mg of a compound of formula (I), a known colchicine derivative and/or a salt thereof once or more times per day.

Preferably, the subject being administered the regimen has atherosclerotic vascular disease, more preferably a coronary disease which may be a stable or unstable coronary disease.

FIGURES

DETAILED DESCRIPTION OF THE INVENTION

General

Figure 1:
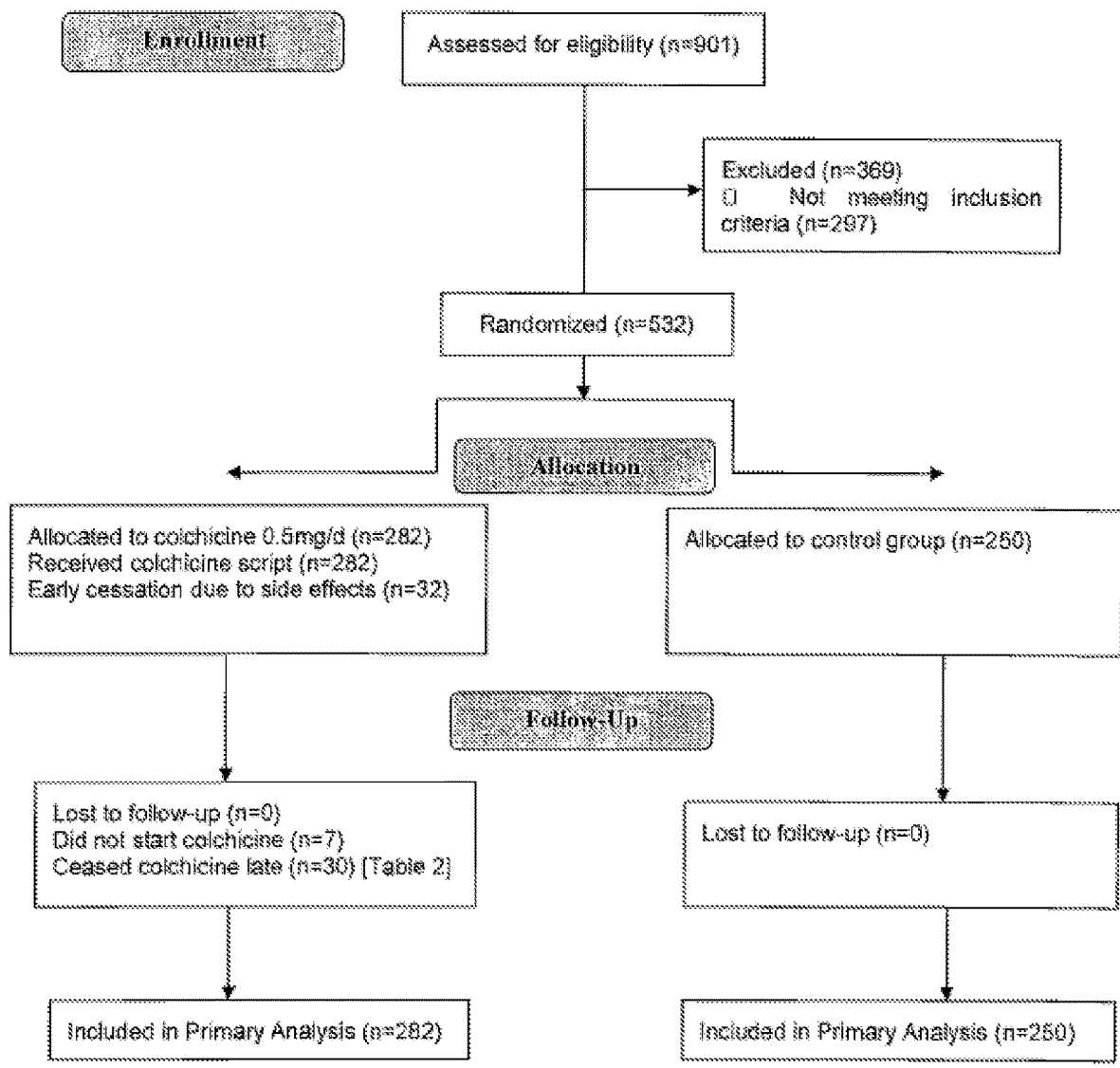
FIG. 1 is a flow chart of the subject enrolment process for Example 1.

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness. Any manufacturer's instructions, descriptions, product specifications, and product sheets for any products mentioned herein or in any document incorporated by reference herein, are hereby incorporated herein by reference, and may be employed in the practice of the invention. No admission is made that any of the references constitute prior art or are part of the common general knowledge of those working in the field to which this invention relates.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (eg. size, displacement and field strength etc). A range of values will be understood to include all values within the range, including the values defining the range, and values adjacent to the range which lead to the same or substantially the same outcome as the values immediately adjacent to that value which defines the boundary to the range.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs. The term "active agent" may mean one active agent, or may encompass two or more active agents.

Throughout this specification, unless the context requires otherwise, the word "comprise" or variations such as "comprises" or "comprising", will be understood to imply the inclusion of a stated integer or group of integers but not the exclusion of any other integer or group of integers.

DETAILED DESCRIPTION

It is well known that consumption of a range of non-steroidal anti-inflammatory agents, such as Vioxx® (rofecoxib), Celebrex® (celecoxib), ibuprofen, Voltaren® (diclofenac), by patients with a previous history of coronary heart disease or other atherosclerotic vascular disease may lead to a significant increase in the risk of further cardiovascular events such as myocardial infarction. Other anti-inflammatory agents such as cortisone can also increase the risk of adverse effects and cardiovascular events in patients with a previous history of coronary heart disease. Despite the anti-inflammatory effects of these agents and their ability to reduce the markers of inflammation (such as a reduction in the levels of c-reactive protein), they are contra-indicated in the treatment of patients with coronary heart disease or other atherosclerotic vascular disease.

In atherosclerotic vascular disease, an artery wall thickens as a result of the accumulation of calcium and fatty materials such as cholesterol. It is a syndrome affecting arterial blood vessels, a chronic inflammatory response in the walls of arteries specifically due to atheromatous plaques. Disruption of the plaques may lead to acute coronary syndrome (including ischemic chest pain, acute myocardial infarction, unstable angina); cardiac arrest; and/or stroke such as non-cardio-embolic ischemic stroke.

Coronary disease and coronary heart disease is a form of atherosclerotic vascular disease caused by plaque building up along the inner walls of the arteries of the heart, which narrows the arteries and reduces blood flow to the heart. Stable coronary diseases are those that occur predictably in intensity, character or frequency at known levels of exertion or other stimuli. Unstable coronary diseases are those that change in intensity, character or frequency.

The inventors of the present invention have surprisingly found that administration of an anti-inflammatory agent within the group of compounds defined by formula (I) may treat or prevent cardiovascular events in patients with atherosclerotic vascular disease such as coronary heart disease.

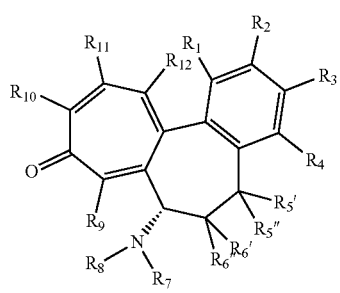

Formula (I)

wherein:

R$_1$, R$_2$, R$_3$, R$_4$, R$_9$, R$_{10}$, R$_{11}$ and R$_{12}$ independently represent hydrogen, C$_{1-4}$ alkyl, C$_{2-4}$ alkenyl, C$_{3-6}$ cycloalkyl, halogen, C$_{1-4}$ haloalkyl, nitro, amino, C$_{2-4}$ acylamino, C$_{1-4}$ alkyl or dialkylamino, hydroxyl, C$_{1-4}$ alkoxy, C$_{1-4}$ alkylthio, a group of the formula —SO$_2$N(R$^x$)$_2$ or SO$_2$R$^x$ where R$^x$ is C$_{1-4}$ alkyl, C$_{1-4}$ acyloxy, or optionally substituted phenyl, optionally substituted phenoxy;

R$_7$ and R$_8$ independently represent hydrogen, C$_{1-4}$ alkyl or C$_{1-4}$ acyl; and R$_5$', R$_5$", R$_6$' and R$_6$" independently represent hydrogen, C$_{1-4}$ alkyl, C$_{2-4}$ alkenyl, C$_{3-6}$ cycloalkyl, halogen, C$_{1-4}$ haloalkyl, nitro, amino, C$_{2-4}$ acylamino, hydroxyl, C$_{1-4}$ alkoxy or C$_{1-4}$ alkylthio a group of the formula —SO$_2$N(R')$_2$ or SO$_2$R$^x$ where R$^x$ is C$_{1-4}$ alkyl, C$_{1-4}$ acyloxy, or optionally substituted phenyl.

In particular, the inventors have discovered that colchicine [N-[(7S)-1,2,3,10-tetramethoxy-9-oxo-5,6,7,9-tetrahydrobenzo[α]heptalen-7-yl]acetamide] may treat or prevent cardiovascular events in patients with atherosclerotic vascular disease such as coronary heart disease.

Certain compounds of formula (I), and methods for their synthesis are described in the following publications, the contents of which are incorporated by reference:

Kouroupis, Pavlos; Hansen, Hans-Jurgen, From Colchicine and Some of Its Derivatives to 1,2,3,9,10-Pentamethoxybenzo[α]heptalenes, Helvetica Chimica Acta; Vol. 78; (1995); p. 1247-1277.

Sun, Li; McPhail, Andrew T.; Hamel, Ernest; Lin, Chii M.; Hastie, Susan B.; et al. Antitumor Agents. 139. Synthesis and Biological Evaluation of Thiocolchicine Analogs 5,6-Dihydro-6(S)-(acyloxy)- and 5,6-Dihydro-6(S)-(aroyloxy)methyl-1,2,3-trimethoxy-9-(methylthio)-8H-cyclohepta[α]naphthalen-8-ones as Novel Cytotoxic and Antimitotic Agents, Journal of Medicinal Chemistry; Vol. 36(5); (1993); p. 544-551

Kouroupis, Pavlos; Kessler, Jacqueline; Hansen, Hans-Juergen, 10-Alkyl-10-demethylcolchicines, Helvetica Chimica Acta; Vol. 79; (1996); p. 208-212.

Chang, Dong-Jo; Jung, Jong-Wha; An, Hongchan; Suh, Young-Ger; Yoon, Eun-Young; Lee, Geon-Bong; Kim, Soon-Ok; Kim, Wan-Joo; Kim, Young-Myeon, Design, synthesis and identification of novel colchicine-derived immunosuppressant, Bioorganic and Medicinal Chemistry Letters; Vol. 19(15); (2009); p. 4416-4420.

Kozaka, Takashi; Nakagawa-Goto, Kyoko; Shi, Qian; Lai, Chin-Yu; Brossi, Arnold; Lee, Kuo-Hsiung; Hamel, Ernest; Bastow, Kenneth F., Antitumor agents 273. Design and synthesis of N-alkyl-thiocolchicinoids as potential antitumor agents, Bioorganic and Medicinal Chemistry Letters; vol. 20(14); (2010); p. 4091-4094.

Danieli, Bruno; Giardini, Alessandra; Lesma, Giordano; Passarella, Daniele; Peretto, Bruno; Sacchetti, Alessandro; Silvani, Alessandra; Pratesi, Graziella; Zunino, Franco, Thiocolchicine-Podophyllotoxin Conjugates: Dynamic Libraries Based on Disulfide Exchange Reaction, Journal of Organic Chemistry; Vol. 71: 7; (2006); p. 2848-2853.

Quinn, Frank R.; Neiman, Zohar; Beisler, John A. Toxicity Quantitative Structure-Activity Relationships of Colchicines Journal of Medicinal Chemistry; Vol. 24(5); (1981); p. 636-639

Bensel, Nicolas; Lagnoux, David; Niggli, Verena; Wartmann, Markus; Reymond, Jean-Louis New C(4)-Functionalized Colchicine Derivatives by a Versatile Multicomponent Electrophilic Aromatic Substitution Helvetica Chimica Acta; Vol. 87(9); (2004); p. 2266-2272

Malysheva, Yulia B.; Fedorov, Alexey Yu.; Combes, Sebastien; Allegro, Diane; Peyrot, Vincent; Knochel, Paul; Gavryushin, Andrei E., Synthesis and biological evaluation of novel anticancer bivalent colchicine-tubulizine hybrids Bioorganic and Medicinal Chemistry; Vol. 20(14); (2012); p. 4271-4278.

Kouroupis, Pavlos; Linden, Anthony; Hansen, Hans-Juergen, Synthesis of 4-Acetylcolchicine Helvetica, Chimica Acta; Vol. 79, (1996); p. 203-207 Bensel, Nicolas; Lagnoux, David; Niggli, Verena; Wartmann, Markus; Reymond, Jean-Louis New C(4)-Functionalized Colchicine Derivatives by a Versatile Multicomponent Electrophilic Aromatic Substitution Helvetica Chimica Acta; Vol. 87(9); (2004); p. 2266-2272.

Chang, Dong-Jo; Jung, Jong-Wha; An, Hongchan; Suh, Young-Ger; Yoon, Eun-Young; Lee, Geon-Bong; Kim, Soon-Ok; Kim, Wan-Joo; Kim, Young-Myeon, Design, synthesis and identification of novel colchicine-derived immunosuppressant, Bioorganic and Medicinal Chemistry Letters; vol. 19; nb. 15; (2009); p. 4416-4420.

Hufford, Charles D.; Capraro, Hans-Georg; Brossi, Arnold. (13)C- and (1)HNMR. Assignments for Colchicine Derivatives, Helvetica Chimica Acta; Vol. 63(1); (1980); p. 50-56.

Nicolaou, K. C.; Valiulin, Roman A.; Pokorski, Jonathan K.; Chang, Vicki; Chen, Jason S., Bio-inspired synthesis and biological evaluation of a colchicine-related compound library, Bioorganic and Medicinal Chemistry Letters; vol. 22; nb. 11; (2012); p. 3776-3780.

Patil, Shivaputra A.; Wang, Jin; Li, Xiaochen S.; Chen, Jianjun; Hosni-Ahmed, Amira; Patil, Renukadevi; Li, Wei; Miller, Duane D.; Jones, Terreia S.; Seibel, William L. New substituted 4H-chromenes as anticancer agents Bioorganic and Medicinal Chemistry Letters; vol. 22; nb. 13; (2012); p. 4458-446.

Nielsen, Kurt; Manchanda, Rajesh Deuterium-enriched colchicines, Thiocolchicine and derivatives thereof; Methods of preparation and use thereof, Patent: US2011/178180; (2011); (A1).

Bartusik, Dorota; Tomanek, Boguslaw; Fallone, Gino; Lattova, Erika; Perreault, Helene; Tuszynski, Jack, Derivatives of thiocolchicine and its applications to CEM cells treatment using 19F Magnetic Resonance ex vivo Bioorganic Chemistry; vol. 38; nb. 1; (2010); p. 1-6.

Alali, Feras Q.; Qandil, Amjad; Gharaibeh, Ahmad A.; Ghawanmeh, Abdullah; Tawaha, Khaled; Burgess, Jason P.; Sy, Arlene; Nakanishi, Yuka; Kroll, David J.; Oberlies, Nicholas H. Colchicinoids from Colchicum crocifolium Boiss. (Colchicaceae) Natural Product Research; vol. 24(2); (2010); p. 152-159.

Boyer, Franois-Didier; Dubois, Joelle; Thoret, Sylviane; Dau, Marie-Elise Tran Huu; Hanna, Issam, Synthesis and tubulin-binding properties of new allocolchicinoids Bioorganic Chemistry; vol. 38(4); (2010); p. 149-158.

Yang, Baiyuan; Zhu, Zhiqing C.; Goodson, Holly V.; Miller, Marvin J. Syntheses and biological evaluation of ring-C modified colchicine analogs, Bioorganic and Medicinal Chemistry Letters; Vol. 20(12); (2010); p. 3831-3833.

Stefely, Jonathan A.; Miller, Patricia A.; Peterson, Rebecca J.; Moraski, Garrett C.; Miller, Marvin J.; Palchaudhuri, Rahul; Hergenrother, Paul J., N-((1-benzyl-1H-1,2,3-triazol-4-yOmethyOarylamide as a new scaffold that provides rapid access to antimicrotubule agents: synthesis and evaluation of antiproliferative activity against select cancer cell lines, Journal of Medicinal Chemistry; Vol. 53(8); (2010); p. 3389-3395.

Kozaka, Takashi; Nakagawa-Goto, Kyoko; Shi, Qian; Lai, Chin-Yu; Brossi, Arnold; Lee, Kuo-Hsiung; Hamel, Ernest; Bastow, Kenneth F. Antitumor agents 273. Design and synthesis of N-alkyl-thiocolchicinoids as potential antitumor agents, Bioorganic and Medicinal Chemistry Letters; Vol. 20.(14); (2010); p. 4091-4094.

Johansson, Emma M. V.; Darbre, Tamis; Reymond, Jean-Louis; Dubois, Joelle, Glycopeptide dendrimer colchicine conjugates targeting cancer cells, Bioorganic and Medicinal Chemistry; Vol. 18(17); (2010); p. 6589-6597.

Dietrich, Andrea; Mueller, Thomas; Schobert, Rainer; Biersack, Bernhard; Effenberger, Katharina; Knauer, Sebastian; 4-(3-Halo/amino-4,5-dimethoxyphenyl)-5-atyloxazoles and-N-methylimidazoles that are cytotoxic against combretastatin a resistant tumor cells and vascular disrupting in a cisplatin resistant germ cell tumor model Journal of Medicinal Chemistry, Vol. 53(18); (2010); p. 6595-6602.

Nicolaus, Norman; Neudoerfl, Joerg-Martin; Schmalz, Hans-Guenther; Zapke, Janet; Oschkinat, Hartmut; Riesterer, Philipp; Prokop, Aram, Azides derived from colchicine and their use in library synthesis: A practical entry to new bioactive derivatives of an old natural drug, ChemMedChem; vol. 5(5) (2010); p. 661-665.

Sharma, Shubhada; Ravindra, Rudravajhala; Blanden, Adam R.; Bane, Susan; Poliks, Barbara; Chiauzzi, Colby Characterization of the colchicine binding site on avian tubulin isotype 131/I, Biochemistry; vol. 49(13); (2010); p. 2932-2942.

Indena S.p.A. "Process for the glycosidation of colchicine and thiocolchicine" Patent: EP2128170; (2009); (A1).

Sun, Tong; Nielsen, Kurt; Watson, Shawn; Hilfiker, Rolf; Sieber, Andreas, Colchicine Solid-State forms: Methods of Making and Methods of Use Thereof, Patent: US2009/312430; (2009); (A1).

Bartusik, Dorota; Tomanek, Boguslaw; Fallone, Gino; Lattova, Erika; Perreault, Helene; Tuszynski, Jack The efficacy of new colchicine derivatives and viability of the TLymphoblastoid cells in three-dimensional culture using 19F MRI and HPLCUV ex vivo, Bioorganic Chemistry; vol. 37(6); (2009); p. 193-201.

Chang, Dong-Jo; Jung, Jong-Who; An, Hongchan; Suh, Young-Ger; Yoon, Eun-Young; Lee, Geon-Bong; Kim, Soon-Ok; Kim, Wan-Joo; Kim, Young Myeong, Design, synthesis and identification of novel colchicine-derived immunosuppressant, Bioorganic and Medicinal Chemistry Letters; vol. 19(15); (2009); p. 4416-4420.

ALBERTA HEALTH SERVICES; Novel Colchicine Derivatives, Methods and Uses Thereof, Patent: WO2011/22805; (2011); (A1)

MUTUAL PHARMACEUTICAL COMPANY, INC.; MANCHANDA, Rajesh, Thiocolchicine Derivatives, method of making and method of use thereof, Patent: WO2010/138670; (2010); (A2)

These publications disclose a large number of compounds derived from colchicine, not all of which fall within the scope of formula (I). Compounds outside the scope of formula (I), yet derived from colchicine and described in the aforementioned publications, are collectively referred to herein as "known colchicine derivatives".

The compounds of formula (I) and the known colchicine derivatives contain at least one asymmetric carbon atom. The methods of the present invention include the use of isolated optical isomers and/or mixtures of such.

The term C1-4 alkyl as used herein means a straight or branched chain alkyl group containing from 1 to 4 carbon atoms, i.e. methyl, ethyl, isopropyl, n-propyl, sbutyl, isobutyl and n-butyl.

The term C1-4 haloalkyl means the abovementioned alkyl groups substituted by one or more halogen atoms, e.g. trifluoromethyl.

The term C1-4 alkoxy and C1-4 alkylthio refer to the abovementioned alkyl groups attached through an oxygen or sulphur atom respectively to the relevant ring.

The term C2-4 alkenyl refers to groups such as vinyl, allyl and butenyl.

The term amino indicates a group of formula —NH2 and also substituted amino groups such as mono-C1-4 alkylamino and di-C1-4 alkyl amino groups.

The term C2-4 acyl amino means an amino group substituted by a C2-4 acyl group such as acetyl.

The term C1-4 alkanoyl refers to groups such as formyl or acetyl.

The term C3-8 cycloalkyl means a saturated ring having from 3 to 8 carbon atoms in the ring, such as cyclopropyl, cyclobutyl, cyclopentyl, cyclohexyl or cyclooctyl.

The term optionally substituted phenyl as used herein means a phenyl group unsubstituted or substituted by one or more groups such as halogen, trifluoromethyl, methyl, methoxy or nitro.

The term optionally substituted phenoxy as used herein means a phenoxy group unsubstituted or substituted by one or more groups such as halogen, trifluoromethyl, methyl, methoxy or nitro.

Therefore, the present invention provides a method for the prevention or treatment of a cardiovascular event in a subject comprising the step of: administering a therapeutically effective amount of a compound of formula (I), a known colchicine derivative and/or a salt thereof.

Preferably, the subject has atherosclerotic vascular disease, more preferably coronary disease, even more preferably clinically stable coronary disease.

Therefore, the invention further provides a method for the prevention or treatment of a cardiovascular event in a subject with atherosclerotic vascular disease comprising the step of: administering a therapeutically effective amount of a compound of formula (I), a known colchicine derivative and/or a salt thereof.

The invention further provides a method for the prevention or treatment of a cardiovascular event in a subject comprising the step of: administering a therapeutically effective amount of a compound of formula (I), a known colchicine derivative and/or a salt thereof, wherein the subject has a coronary disease prior to administration of the therapeutically effective amount of a compound of formula (I), a known colchicine derivative and/or a salt thereof. Preferably the coronary disease is a stable coronary disease.

The method may include the further step of co-administering a second agent for the treatment and/or prevention of a cardiovascular event in a subject. For example, the composition delivered in the method may further include an agent for anti-platelet therapy. Such anti-platelet therapy agents include: Irreversible cyclooxygenase inhibitors (such as Aspirin); Adenosine diphosphate (ADP) receptor inhibitors (such as Clopidogrel (Plavix®), Prasugrel (Effient®), Ticagrelor (Brilinta®), Ticlopidine (Ticlid®), Cangrelor); Phosphodiesterase inhibitors (such as Cilostazol (Pletal®)); Glycoprotein IIB/IIIA inhibitors (such as Abciximab (ReoPro®), Eptifibatide (Integrilin®), Tirofiban (Aggrastat®)); Adenosine reuptake inhibitors (such as Dipyridamole (Persantine®)); Thromboxane inhibitors including Thromboxane synthase inhibitors and Thromboxane receptor antagonists (such as Terutroban).

Additionally, the composition delivered in the method may include one or more statins. Statins that may be used in the composition of the present invention include: simvastatin, atorvastatin, fluvastatin, lovastatin, pitavastatin, pravastatin, and rosuvastatin.

The additional statin and/or anti-platelet agent may be administered at the same time as the compound of formula (I), a known colchicine derivative and/or a salt thereof, for example as tablets or capsules taken at the same time as each other; within an hour of each other; within 2 hours, 4 hours, 6 hours, 8 hours or 12 hours of each other; or within a day of each other. Alternatively, the additional statin and/or anti-platelet agent may be in the same dosage form (for example the same tablet or capsule) as the compound of formula (I), a known colchicine derivative and/or a salt thereof.

The invention therefore provides a method for the prevention or treatment of a cardiovascular event in a subject with atherosclerotic vascular disease comprising the step of: administering a therapeutically effective amount of a compound of formula (I), a known colchicine derivative and/or a salt thereof and one or more additional agents selected from the list comprising: a statin or an anti-platelet agent.

Preferably the atherosclerotic vascular disease is a coronary disease, which may be a clinically stable coronary disease or an unstable coronary disease.

In one form of the invention, the methods comprise the administration of a compound of formula (I).

In one form of the invention, the methods comprise the administration of a compound selected from the group of compounds described in one or more of the publications listed above as defining known colchicine derivatives.

In a preferred form of the invention, the compound of formula (I) has one or more of the following features:
$R_1$, $R_2$, $R_3$, $R_4$, $R_9$, $R_{10}$, $R_{11}$ and $R_{12}$ independently represent hydrogen, $C_{1-4}$ alkyl, $C_{2-4}$ alkenyl, $C_{3-6}$ cycloalkyl, halogen, $C_{1-4}$ haloalkyl, nitro, amino, $C_{2-4}$ acylamino, hydroxyl, $C_{1-4}$ alkoxy, $C_{1-4}$ alkylthio, a group of the formula —$SO_2N(R^x)_2$ or $SO_2R^x$ where $R^x$ is $C_{1-4}$ alky;
$R_5'$, $R_5''$, $R_6'$ and $R_6''$ independently represent hydrogen, $C_{1-4}$ alkyl, $C_{2-4}$ alkenyl, $C_{3-6}$ cycloalkyl, halogen, $C_{1-4}$ haloalkyl, nitro, amino, $C_{2-4}$ acylamino, hydroxyl, $C_{1-4}$ alkoxy or $C_{1-4}$ alkylthio a group of the formula —$SO_2N(R^x)_2$ or $SO_2R^x$ where $R^x$ is $C_{1-4}$ alkyl.

In a preferred form of the invention, the compound of formula (I) has one or more of the following features:
a. At least one of $R_1$, $R_2$ and $R_3$ is $C_{1-4}$ alkoxy or $C_{1-4}$ alkylthio;
b. At least one of $R_7$ and $R_8$ is $C_{2-4}$ acyl;
c. $R_{10}$ is $C_{1-4}$ alkoxy or $C_{1-4}$ alkylthio In a preferred form of the invention, the compound of formula (I) has two or more of the above-mentioned features.

In a preferred form of the invention, the compound of formula (I) has each of the abovementioned features.

In a more preferred form of the invention, the compound of formula (I) has the following feature:
d. Each of $R_4$, $R_5'$, $R_5''$, $R_6'$, $R_6''$ $R_{11}$, $R_{12}$ is H.

In a more preferred form of the invention, the compound of formula (I) has the following feature:
e. one of $R_7$ and $R_8$ is H, and the other is $C_{2-4}$ acyl.

Thus, in a highly preferred form of the invention, the compound of formula (I) has each of the following features:

a. At least one of $R_1$, $R_2$ and $R_3$ is $C_{1-4}$ alkoxy or $C_{1-4}$ alkylthio;
b. At least one of $R_7$ and $R_8$ is $C_{2-4}$ acyl;
c. $R_{10}$ is $C_{1-4}$ alkoxy or $C_{1-4}$ alkylthio;
d. Each of $R_4$, $R_5'$, $R_5''$, $R_6'$, $R_6''$ $R_{11}$, $R_{12}$ is independently H;
e. One of $R_7$ and $R_8$ is H, and the other $C_{2-4}$ acyl.

Generally, $C_{1-4}$ alkoxy is preferred over $C_{1-4}$ alkylthio.
Generally, $C_{1-2}$ alkoxy is preferred over $C_{3-4}$ alkoxy.
In a preferred form of the invention, the compound of formula (I) is selected from the group of compounds defined by the following features:
$R_1$, $R_2$, $R_3$, and, $R_{10}$, $R_{11}$ independently represent $C_{1-4}$ alkoxy or $C_{1-4}$ alkylthio;
$R_7$ and $R_8$ independently represent hydrogen or $C_{2-4}$ acyl; and
$R_4$, $R_5'$, $R_5''$, $R_6'$ and $R_6''$ independently represent hydrogen or $C_{1-4}$ alkyl.

Preferably, $R_1$, $R_2$, $R_3$, and, $R_{10}$, $R_{11}$ independently represent $C_{1-4}$ alkoxy.

Preferably still, each of $R_1$, $R_2$, $R_3$, and, $R_{10}$, $R_{11}$ represent $C_{1-4}$ alkoxy.

Preferably $R_4$, $R_5'$, $R_5''$, $R_6'$ and $R_6''$ independently represent hydrogen.

Preferably still, each of $R_4$, $R_5'$, $R_5''$, $R_6'$ and $R_6''$ represent hydrogen.

In a highly preferred form of the invention, the compound of formula (I) has the following features:
each of $R_1$, $R_2$, $R_3$, and, $R_{10}$, $R_{11}$ represent $C_1$ alkoxy;
each of $R_4$, $R_5'$, $R_5''$, $R_6'$ and $R_6''$ represent H;
$R_7$ represents H; and
$R_8$ represents C2 acyl;
such that the compound of formula (I) is colchicine.

Compounds of formula (I) of the invention are useful in both free base or acid addition salt forms. The acid addition salts are preferably the pharmaceutically acceptable, non-toxic addition salts with suitable acids, such as those with inorganic acids, for example hydrochloric hydrobromic, nitric, sulfuric and phosphoric acids, or with organic acids, such as organic carboxylic acids, for example glycolic, maleic, hydroxymaleic, fumaric, malic, tartaric, citric, salicylic, o-acetoxybenzoic, nicotinic or isonicotinic acid, or organic sulfonic acids for example methanesulfonic, ethane sulfonic, 2-hydroxyethanesulfonic, toluene-p-sulfonic or naphthalene-2-sulfonic acid.

Without wishing to be bound by any one theory, we believe the activity of a compound of formula (I), a known colchicine derivative and/or a salt thereof in relation to the prevention of vascular events in patients with coronary disease may be due to the inhibition of neutrophil function, leading to a reduction in the risk of plaque instability and thus the risk of de novo vascular events due to disruption of native atherosclerotic plaques in patients with atherosclerotic vascular disease such as coronary disease. For example, the colchicine may be preventing activation and amplification of the [cholesterol] crystal induced inflammation within atherosclerotic plaques and thereby acting to slow the progression of atherosclerosis and promote the stability of atherosclerotic plaques.

There is therefore provided a method for reducing or preventing cholesterol crystal induced inflammation within atherosclerotic plaques in a subject, comprising the step of administering a dosage of 0.5 mg or 0.6 mg of a compound of formula (I), a known colchicine derivative and/or a salt thereof.

Preferably the subject with atherosclerotic plaques has atherosclerotic vascular disease, more preferably a stable or unstable coronary disease.

Preferably the composition administered to reduce or prevent cholesterol crystal induced inflammation within atherosclerotic plaques further comprises one or more additional agents selected from the list comprising: a statin and/or an antiplatelet agent.

Preferably, the method of treatment of the present invention results in the treatment or prevention of one or more of the following cardiovascular events: acute coronary syndrome (including ischemic chest pain, acute myocardial infarction, unstable angina); cardiac arrest; or stroke such as non-cardio-embolic ischemic stroke.

Generally, the terms "treat", "treating" and "treatment" and derivatives used herein have the meaning to affect a subject, tissue or cell to produce a desired pharmacological and/or physiological effect. The treatment may be therapeutic in terms of: preventing progression of the coronary disease or other atherosclerotic vascular disease and cardiovascular events; or causing a partial or complete cure and/or regression of the coronary disease or other atherosclerotic vascular disease and cardiovascular events.

"Preventing" or "prevention" and derivative terms relate to the partial or complete prevention or at least delaying the onset of the development of coronary disease or other atherosclerotic vascular disease and cardiovascular events or the symptoms thereof in a subject who: has not yet been diagnosed with coronary disease or other atherosclerotic vascular disease or had a cardiovascular event; has had coronary disease and may be in remission and wishes to prevent re-occurrence of the coronary disease and/or cardiovascular event; or has been diagnosed as being at risk of developing coronary disease or other atherosclerotic vascular disease and having a cardiovascular event.

The invention further provides for the use of a compound of formula (I), a known colchicine derivative and/or a salt thereof in the preparation of a medicament for the treatment or prevention of a cardiovascular event.

The invention also provides for the use of a therapeutically effective amount of a compound of formula (I), a known colchicine derivative and/or a salt thereof in the preparation of a medicament for the prevention or treatment of a cardiovascular event in a subject with atherosclerotic vascular disease.

Preferably the atherosclerotic vascular disease is a clinically stable coronary disease or unstable coronary disease.

There is also provided the use of a therapeutically effective amount of a compound of formula (I), a known colchicine derivative and/or a salt thereof in the preparation of a medicament for reducing or preventing cholesterol crystal induced inflammation within atherosclerotic plaques in a subject.

The invention further provides for the use of a therapeutically effective amount of a compound of formula (I) in the preparation of a medicament for the prevention or treatment of a cardiovascular event in a subject.

In another form of the invention, there is provided the use of a therapeutically effective amount of a compound selected from the group of compounds described in one or more of the publications listed above as defining known colchicine derivatives in the preparation of a medicament for the prevention or treatment of a cardiovascular event in a subject.

Preferably, the medicament discussed above comprises between 0.01 and 1 mg of a compound of formula (I), a known colchicine derivative and/or a salt thereof; between 0.05 and 0.95 mg, between 0.1 and 0.9 mg, between 0.2 and 0.8 mg, or between 0.4 and 0.7 mg. More preferably, it comprises between 0.5 mg and 0.6 mg of a compound of formula (I), a known colchicine derivative and/or a salt thereof, most preferably either 0.5 mg or 0.6 mg.

The present invention further provides a composition for the prevention or treatment of a cardiovascular event in a subject, the composition comprising a therapeutically effective amount of a compound of formula (I), a known colchicine derivative and/or a salt thereof and one or more pharmaceutically acceptable additives, excipients carriers and/or diluents.

The present invention further provides a composition for reducing or preventing cholesterol crystal induced inflammation within atherosclerotic plaques in a subject, the composition comprising a therapeutically effective amount of a compound of formula (I), a known colchicine derivative and/or a salt thereof and one or more pharmaceutically acceptable additives, excipients carriers and/or diluents.

Preferably, the composition comprising a compound of formula (I), a known colchicine derivative and/or a salt thereof comprises between 0.01 and 1 mg of a compound of formula (I), a known colchicine derivative and/or a salt thereof; between 0.05 and 0.95 mg, between 0.1 and 0.9 mg, between 0.2 and 0.8 mg, or between 0.4 and 0.7 mg. More preferably, it comprises between 0.5 mg and 0.6 mg of a compound of formula (I), a known colchicine derivative and/or a salt thereof, most preferably either 0.5 mg or 0.6 mg.

The exact amount of the a compound of formula (I), a known colchicine derivative and/or a salt thereof in the composition will of course, depend on the route of delivery, the nature of the coronary heart disease or other atherosclerotic vascular disease, the therapeutically effective amount of colchicine required and the general nature and health of the subject to whom the composition is delivered.

Preferably the concentration of the a compound of formula (I), a known colchicine derivative and/or a salt thereof in the composition will be of sufficient strength (qs) to provide a therapeutically effective dose to the target cells. Such therapy may be directed to the treatment or prevention of a cardiovascular event in a subject. More preferably, the therapeutically effective dose is directed to the treatment or prevention of a cardiovascular event in a subject who has atherosclerotic vascular disease such as stable or unstable coronary disease.

The compositions of the present invention, comprising a compound of formula (I), a known colchicine derivative and/or a salt thereof, are preferably adapted to be delivered to the subject in need more than once daily, once daily or less often. For example, if the composition is adapted for oral delivery, the composition is preferably administered once a day. However, it is contemplated that the composition can be administered more frequently than this (for example, two or three times a day) or less often (for example every second day, every third day, once a week). Alternatively, if the composition comprising a compound of formula (I), a known colchicine derivative and/or a salt thereof is in the form of an injectable formulation, it is preferable that the composition be adapted for delivery once a week, or once a month.

The compositions may further comprise and one or more additional agents selected from the list comprising: a statin and/or an anti-platelet agent.

As used herein, the term "therapeutically effective amount" means an amount of a compound of formula (I), a known colchicine derivative and/or a salt thereof effective to yield a desired therapeutic response, for example to prevent or treat a cardiovascular event in a subject. The specific therapeutically effective amount will of course vary with such factors as the particular condition being treated, the physical condition and clinical history of the subject, the type of animal being treated, the duration of the treatment, the nature of concurrent therapy (if any), the specific formulations employed and the structure of the composition.

The term "pharmaceutically", "physiologically", or "veterinary acceptable" as used herein refers to pharmaceutically active agents, physiologically active agents, veterinary active agents, or inert ingredients which are suitable for use in oral formulations or formulations designed for contact with the skin of animals, including humans, without undue toxicity, incompatibility, instability, irritation, allergic response, and the like, commensurate with a reasonable benefit/risk ratio.

Additives, excipients carriers and diluents for use in the compositions of the present invention include, without limitation: water, saline, ethanol, dextrose, glycerol, glycerol and polyhydric alcohols, milk protein, vitamins, animal and vegetable oils, polyethylene glycols, lactose, dextrose, sucrose sorbitol, mannitol and other sugars, starches, gum acacia, calcium phosphates, alginate, tragacanth, gelatine, calcium silicate, cellulose and its derivatives such as microcrystalline cellulose and methyl cellulose, polyvinylpyrrolidone, water syrup, methyl and propylhydroxybenzoates, talc, magnesium carbonate, titanium dioxide, magnesium stearate and mineral oil or combinations thereof.

The compositions can additionally include lubricating agents, dispersion media, pH buffering agents, wetting agents, emulsifying and suspending agents, solvents, preserving agents, sweetening agents or flavouring agents, antifoaming agents, polymers, antioxidants, chelating agents, viscomodulators, tonicifiers, flavorants, colorants, odorants, opacifiers, suspending agents, binders, fillers, plasticizers, lubricants, absorption-promoting agents and mixtures thereof. Preservatives include antimicrobial, antibacterial and antifungal agents, antioxidants, chelating agents and inert gases. The particular selection of constituent that can be included in the compositions described herein will generally depend on the type of preparation.

In the preferred embodiments, the composition is formulated to enable ready location and retention of the compound of formula (I), a known colchicine derivative and/or a salt thereof in the area required to deliver the therapeutic effect while at the same time not significantly interfering with the compound's efficacy. It will be understood, therefore, that the therapeutically effective composition may be formulated differently based on the area of treatment and how the composition is to be administered.

There are a range of reference sources for the development of pharmaceutical compositions which may be referred to by the skilled person when developing formulations comprising colchicine, such as "Remington's Pharmaceutical Sciences", 21st Edition (2009), Mack Publishing Company, Easton, Pennsylvania, USA, all the contents of which are incorporated herein.

A composition comprising a compound of formula (I), a known colchicine derivative and/or a salt thereof may be administered using standard procedures, for example: orally, topically, parenterally, intraorbitally, ophthalmically, intraventricularly, intracranially, intracapsularly, intraspinally, intracisternally, intraperitoneally, buccally, rectally, vaginally, intranasally, or by aerosol administration and/or inhalation spray or via an implanted reservoir.

In a preferred embodiment the compound of formula (I), a known colchicine derivative and/or a salt thereof is administered internally for the treatment or prevention of a cardiovascular event in a subject. For example, the compound may be delivered by oral routes in the form of a tablet, capsule, liquid dose, gel or powder; by injection e.g. into the blood stream, muscle tissue or directly into an organ such as the heart; by sublingual, buccal, rectal or intravaginal delivery; or by inhalation.

Pharmaceutically acceptable carriers, adjuvants and vehicles that may be used in oral, parenteral, sublingual, buccal, rectal or intravaginal or inhaled compositions may include: ion exchangers; alumina; aluminum stearate; lecithin; self-emulsifying drug delivery systems such as alpha-tocopherol polyethylene glycol 1000 succinate, or other similar polymeric delivery matrices or systems such as nanoparticles; serum proteins such as human serum albumin; buffer substances such as phosphates; glycine; sorbic acid; potassium sorbate; partial glyceride mixtures of saturated vegetable fatty acids; water; salts or electrolytes, such as protamine sulfate, disodium hydrogen phosphate, potassium hydrogen phosphate, sodium chloride, zinc salts; colloidal silica; magnesium trisilicate; polyvinyl pyrrolidone; cellulose-based substances; polyethylene glycol; sodium carboxymethylcellulose; polyacrylates; polyethylene-polyoxypropylene-block polymers; and wool fat.

The composition of the present invention comprising a compound of formula (I), a known colchicine derivative and/or a salt thereof can further contain one or more additives, provided that they do not detrimentally affect the therapeutic effect afforded by the compound of formula (I), a known colchicine derivative and/or a salt thereof. In one embodiment, the additive is a colorant. In alternative embodiments, the additive is a preservative such as a mould inhibitor or an anti-oxidant, a fragrance, or a stabiliser. The additional additives may also be agents that render the composition an emulsion, a micro-emulsion or a nano-emulsion.

In a preferred embodiment, the compound of formula (I), a known colchicine derivative and/or a salt thereof is delivered via an oral route. The colchicine may therefore be in the form of a tablet, capsule, gel or liquid composition. If the compound of formula (I), a known colchicine derivative and/or a salt thereof is in the form of a tablet, the tablet may further comprise fillers such as: lactose (milk sugar), microcrystalline cellulose, corn starch, sugars (including sucrose, mannitol, sorbitol, fructose, and dextrose), whey and yeast; and/or binders such as: povidone, xanthan gum and Carbopol. Additional ingredients may be in the form of: disintergrants such as crospovidone, croscarmellose sodium, and gellan gum; coatings such as shellac; lubricants such as magnesium stearate, stearic acid, sodium stearyl fumarate and hydrogenated vegetable oil; colorants such as titanium dioxide and iron oxides; flavours (in chewable tablets); and plasticizers. Most preferably, the compound of formula (I), a known colchicine derivative and/or a salt thereof is administered in the form of a tablet comprising colchicine, magnesium stearate, lactose, maize starch and povidone. Preferably, the tablet, capsule, gel or liquid composition comprises between 0.01 and 1 mg of a compound of formula (I), a known coichicine derivative and/or a salt thereof; between 0.05 and 0.95 mg, between 0.1 and 0.9 mg, between 0.2 and 0.8 mg, or between 0.4 and 0.7 mg. More preferably, it comprises between 0.5 mg and 0.6 mg of a compound of formula (I), a known coichicine derivative and/or a salt thereof, most preferably either 0.5 mg or 0.6 mg.

Alternatively, the compound of formula (I), a known coichicine derivative and/or a salt thereof may be delivered via sublingual, buccal, rectal or intravaginal delivery, for example by administration of a tablet, capsule, gel, powder or spray.

In another embodiment, the compound of formula (I), a known colchicine derivative and/or a salt thereof is delivered parenterally, preferably by injection, for example subcutaneously or intramuscularly. However, delivery may also be intra-arterially or intraperitoneally for the treatment or prevention of a cardiovascular event in a subject. The composition may be in the form of a sterile injectable preparation, for example, as a sterile injectable suspension for the treatment or prevention of a cardiovascular event in a subject. This suspension may be formulated according to techniques known in the art using suitable dispersing agents, surfactants, and suspending agents (e.g. Tween 80). The sterile injectable preparation may also be a sterile injectable solution or suspension in a non-toxic parenterally-acceptable diluent or solvent (e.g. 1, 2-propanediol). Acceptable vehicles and solvents may include mannitol, water, Ringers solution and isotonic sodium chloride solution with buffer. Furthermore, sterile, fixed oils may be employed as a solvent or a suspending medium. For this purpose, any bland fixed oil may be employed including mono- or diglycerides. Fatty acids, such as oleic acid and its glyceride derivatives, and natural pharmaceutically acceptable oils, such as polyoxyethylated olive oil or castor oil, may also be used in the preparation of injectables. Preferably, the injectable composition comprises between 0.01 and 1 mg of a compound of formula (I), a known coichicine derivative and/or a salt thereof; between 0.05 and 0.95 mg, between 0.1 and 0.9 mg, between 0.2 and 0.8 mg, or between 0.4 and 0.7 mg. More preferably, it comprises between 0.5 mg and 0.6 mg of a compound of formula (I), a known colchicine derivative and/or a salt thereof, most preferably either 0.5 mg or 0.6 mg.

The composition may further comprise a second agent for the treatment and/or prevention of a cardiovascular event in a subject. For example, the composition may further include an agent for in anti-platelet therapy. Such antiplatelet therapy agents include: Irreversible cyclooxygenase inhibitors (such as Aspirin); Adenosine diphosphate (ADP) receptor inhibitors (such as Clopidogrel (Plavix®), Prasugrel (Effient®), Ticagrelor (Brilinta®), Ticlopidine (Ticlid®), Cangrelor); Phosphodiesterase inhibitors (such as Cilostazol (Pletal®)); Glycoprotein IIB/IIIA inhibitors (such as Abciximab (ReoPro®), Eptifibatide (Integrilin®), Tirofiban (Aggrastat®)); Adenosine reuptake inhibitors (such as Dipyridamole (Persantine®)); Thromboxane inhibitors including Thromboxane synthase inhibitors and Thromboxane receptor antagonists (such as Terutroban).

Additionally, the composition may include one or more statins. Statins that may be used in the composition of the present invention include: simvastatin, atorvastatin, fluvastatin, lovastatin, pitavastatin, pravastatin, and rosuvastatin.

The present invention also provides a regimen for the treatment or prevention of a cardiovascular event in a subject, the regimen comprising the step of:

administering a dosage of 0.5 mg or 0.6 mg of a compound of formula (I), a known colchicine derivative and/or a salt thereof once or more per day.

The present invention also provides a regimen for reducing or preventing cholesterol crystal induced inflammation within atherosclerotic plaques in a subject, the regimen comprising the step of:

administering a dosage of 0.5 mg or 0.6 mg of a compound of formula (I), a known colchicine derivative and/or a salt thereof once or more per day.

Alternatively, the regimen may involve administering the compound of formula (I), a known colchicine derivative and/or a salt thereof every second day, every third day, every fourth day, every fifth day, every sixth day or once a week.

Preferably, the subject being administered the regimen has atherosclerotic vascular disease, preferably a stable coronary disease.

The regimen may include the additional step of co-administering one or more additional agents selected from the list comprising: a statin and/or an antiplatelet agent. The one or more additional agents may also be administered once per day.

Methods for synthesising compounds of formula (I) and/or known colchicine derivatives may be found in the following publications, the contents of which are hereby incorporated by reference.

Substitution at $R_1$, $R_2$, $R_3$, $R_4$

1. Synthesis of Colchicine Derivatives Containing an Methoxyl:

Chang, Dong-Jo; Jung, Jong-Wha; An, Hongchan; Suh, Young-Ger; Yoon, Eun-Young; Lee, Geon-Bong; Kim, Soon-Ok; Kim, Wan-Joo; Kim, Young-Myeon, Design, synthesis and identification of novel colchicine-derived immunosuppressant, Bioorganic and Medicinal Chemistry Letters; vol. 19; nb. 15; (2009); p. 4416-4420.

Hufford, Charles D.; Capraro, Hans-Georg; Brossi, Arnold. (13)C- and (1)H-NMR. Assignments for Colchicine Derivatives, Helvetica Chimica Acta; Vol. 63(1); (1980); p. 50-56.

2. Synthesis of Colchicine Derivatives Having Substituent at $R_4$:

Bensel, Nicolas; Lagnoux, David; Niggli, Verena; Wartmann, Markus; Reymond, Jean-Louis New C(4)-Functionalized Colchicine Derivatives by a Versatile Multicomponent Electrophilic Aromatic Substitution Helvetica Chimica Acta; Vol. 87(9); (2004); p. 2266-2272.

3. Synthesis of Colchicine Derivative Containing a Containing an Acetyl Functional Group at $R_4$:

Kouroupis, Pavlos; Linden, Anthony; Hansen, Hans-Juergen, Synthesis of 4-Acetylcolchicine Helvetica, Chimica Acta; Vol. 79, (1996); p. 203-207:

Substitution at $R_8$ or $R_7$

1. Synthesis of colchicine derivatives containing an azide group: Malysheva, Yulia B.; Fedorov, Alexey Yu.; Combes, Sebastien; Allegro, Diane; Peyrot, Vincent; Knochel, Paul; Gavryushin, Andrei E., Synthesis and biological evaluation of novel anticancer bivalent colchicine-tubulizine hybrids Bioorganic and Medicinal Chemistry; Vol. 20(14); (2012); p. 4271-4278.

2. Synthesis of Colchicine Derivatives Containing an Amide Group:

Bensel, Nicolas; Lagnoux, David; Niggli, Verena; Wartmann, Markus; Reymond, Jean-Louis New C(4)-Functionalized Colchicine Derivatives by a Versatile Multicomponent Electrophilic Aromatic Substitution Helvetica Chimica Acta; Vol. 87(9); (2004); p. 2266-2272

Substitution at $R_{10}$

1. Synthesis of Colchicine Derivative Containing a Thio Group.

Kozaka, Takashi; Nakagawa-Goto, Kyoko; Shi, Qian; Lai, Chin-Yu; Brossi, Arnold; Lee, Kuo-Hsiung; Hamel, Ernest; Bastow, Kenneth F., Antitumor agents 273. Design and synthesis of N-alkyl-thiocolchicinoids as potential antitumor agents, Bioorganic and Medicinal Chemistry Letters; vol. 20(14); (2010); p. 4091-4094.

Danieli, Bruno; Giardini, Alessandra; Lesma, Giordano; Passarella, Daniele; Peretto, Bruno; Sacchetti, Alessandro; Silvani, Alessandra; Pratesi, Graziella; Zunino, Franco, Thiocolchicine-Podophyllotoxin Conjugates: Dynamic Libraries Based on Disulfide Exchange Reaction, Journal of Organic Chemistry; Vol. 71: 7; (2006); p. 2848-2853.

Quinn, Frank R.; Neiman, Zohar; Beisler, John A. Toxicity Quantitative Structure-Activity Relationships of Colchicines Journal of Medicinal Chemistry; Vol. 24(5); (1981); p. 636-639

2. Synthesis of Colchicine Derivative Containing an Haloalkyl Functional Group.

Chang, Dong-Jo; Jung, Jong-Wha; An, Hongchan; Suh, Young-Ger; Yoon, Eun-Young; Lee, Geon-Bong; Kim, Soon-Ok; Kim, Wan-Joo; Kim, Young-Myeon, Design, synthesis and identification of novel colchicine-derived immunosuppressant, Bioorganic and Medicinal Chemistry Letters; Vol. 19(15); (2009); p. 4416-4420.

3. Synthesis of Colchicine Derivative Containing an Alkoxy Group.

Kouroupis, Pavlos; Kessler, Jacqueline; Hansen, Hans-Juergen, 10-Alkyl-10-demethylcolchicines, Helvetica Chimica Acta; Vol. 79; (1996); p. 208-212.

4. Synthesis of Colchicine Derivative Containing an Hydroxyl Group.

Kouroupis, Pavlos; Hansen, Hans-Jurgen, From Colchicine and Some of Its Derivatives to 1,2,3,9,10-Pentamethoxybenzo[a]heptalenes, Helvetica Chimica Acta; Vol. 78; (1995); p. 1247-1277.

Sun, Li; McPhail, Andrew T.; Hamel, Ernest; Lin, Chii M.; Hastie, Susan B.; et al. Antitumor Agents. 139. Synthesis and Biological Evaluation of Thiocolchicine Analogs 5,6-Dihydro-6(S)-(acyloxy)- and 5,6-Dihydro-6(S)-(aroyloxy)methyl-1,2,3-trimethoxy-9-(methylthio)-8H-cyclohepta[α]naphthalen-8-ones as Novel Cytotoxic and Antimitotic Agents, Journal of Medicinal Chemistry; Vol. 36(5); (1993); p. 544-551.

EXAMPLES

The following examples are provided to further illustrate several embodiments of the invention.

Example 1

A prospective randomized observer blinded end-point trial was conducted to determine whether adding 0.5 mg/day of colchicine to standard secondary prevention therapies including aspirin and high dose statins reduces the risk of cardiovascular events in patients with objectively diagnosed and clinically stable coronary disease.

Methods

Study Conduct and Design: The LoDoCo Trial was conducted under the auspices of the Heart Research Institute of Western Australia. It was designed by the principal investigators, registered with the Australian Clinical Trial Registry [12610000293066], and received ethics approval from the Human Research Ethics Committee at Sir Charles Gairdner Hospital Perth Western Australia in July 2008. There was no external funding source.

We employed a PROBE [Prospective Randomized, Open, Blinded End-point] design [8] Eligible consenting patients with established coronary disease presenting for routine clinical review were randomized to receive colchicine 0.5 mg/day or no colchicine without any other change to their medical therapy. All outcomes were evaluated by an experienced adjudicator blinded to the treatment allocation.

Study Size and Eligibility: It was planned to recruit a study population that would include 250 patients randomized to the control group and 250 patients randomized to treatment who were tolerant of colchicine for at least 4 weeks after the date of their randomization.

Patients were eligible for inclusion if they met each of the following criteria: 1] angiographically proven coronary disease; 2] aged 35 to 85 years; 3] clinically stable for at least 6 months, 4] no major competing co-morbidities or contraindication to colchicine therapy, 5] considered to be compliant with therapy and attending routine cardiology follow up appointments, and 6] willing to be consented and randomized into the study. Patients with a history of bypass surgery were only eligible if they had undergone bypass surgery more than 10 years before, or had angiographic evidence of graft failure or had undergone stenting since their bypass surgery. All patients signed informed consent before randomization.

Randomization: The randomization sequence was computer generated, kept concealed from the investigators at all times and was managed by a research assistant who had no involvement in the evaluation or management of study patients. Once the assistant received the consent form, the patients' demographic data were entered into the data base and the investigators and patients were advised in writing of the treatment group to which the patient had been assigned.

Despite electing to use the lowest dose of colchicine available, it was anticipated that a number of patients would withdraw from therapy early after randomization due to gastrointestinal side effects. In order to ensure that the requisite number of patients in the treatment arm were actually tolerant of treatment, the protocol allowed for the research assistant to assign a newly recruited patient to treatment if a patient discontinued colchicine due to side effects in the first month. Patients who were intolerant to therapy remained in the study, and were followed in the usual manner and included in the primary intention to treat analysis.

Intervention: Patients randomized to active treatment were given a prescription for colchicine 0.5 mg daily by their referring cardiologist. The drug was dispensed by their usual chemist, and if requested, patients were reimbursed for the cost of these scripts. All other treatments were continued as usual.

Follow-up and definition of clinical outcomes: Patient compliance with treatment and outcome data were collected at routine follow up visits and at the time of any unplanned hospital admission.

An acute coronary syndrome (ACS) was defined as either [α] Acute Myocardial Infarction (AMI), as evidenced by acute ischemic chest pain associated with a rise in serum troponin above the upper limit of normal [9] or [b] Unstable Angina (UA), as evidenced by a recent acceleration of the patients angina unassociated with a rise in serum troponin but associated with angiographic evidence of a change in the patient's coronary anatomy. (Unstable Angina Braunwald classification types IB and IIB) [10]. The ACS was characterized as being stent-related if there was evidence of significant in-stent stenosis or acute stent thrombosis. Out of Hospital Cardiac Arrest was defined as either a sudden death as evidenced on the patients' death certificate, or a non-fatal out of hospital cardiac arrest, defined as a recovery from sudden collapse associated with documented asystole, ventricular tachycardia or ventricular fibrillation. Noncardioembolic ischemic stroke was defined as CT or MRI proven ischemic stroke adjudged by the treating neurologist as not being due to atrial fibrillation or intracranial hemorrhage.

The primary efficacy outcome was the composite, ACS, fatal or non-fatal out of hospital cardiac arrest or non-cardio-embolic ischemic stroke.

Secondary outcomes were [a] individual components of the primary outcome, and [b] the components of ACS unrelated to stent disease.

Timelines: The pre-specified study duration was a minimum follow up of two years in all patients. Accordingly the study was closed on May 31, 2012. During May, all living patients were contacted by phone to collect compliance and outcome data from the last date of follow-up. Final outcome data were available in all patients and no patients were lost to follow up.

Statistical Power: Assuming that the control group had a combined event rate [ACS, out of hospital cardiac arrest or non cardio-embolic-ischemic stroke] of 8% [11], an accrual interval of 2 years and a follow-up after the accrual interval of 2 years, the planned sample size provided >80% power to detect a hazard ratio of <0.50 based on a two sided significance level of 5%.

Data analysis: Summary statistics, including mean and standard deviation were calculated for all baseline characteristics by treatment arm. All time to event outcomes were calculated in days by subtracting the date of randomization from either: (1) the date of event or death; or (2) the trial termination date for those patients not experiencing the defined event.

As pre-specified, the primary efficacy analysis was based on the intention-to-treat principle. The intention-to-treat analysis included all randomized subjects and all events during the time from randomization to the trial termination. Trial termination date was fixed as May 31, 2012. A secondary pre-specified on treatment analysis was also performed, based on patients who were both tolerant and compliant to therapy beyond the first month of randomization. All events during the time from randomisation until non-compliance with colchicine treatment regimen were included in this analysis.

The time-to-first-event for all outcomes is presented using a Kaplan-Meier plot.

The primary efficacy outcome was analysed using a cox proportional hazards model including treatment group coded as control or colchicine. The secondary outcomes were analysed similarly. In addition, the primary analysis was stratified by gender, age, diagnosis of diabetes, past myocardial infarction, unstable angina, coronary bypass surgery, coronary angioplasty, and therapy with aspirin, clopidogrel or both, high dose statin therapy (defined as a dose of statin equivalent to atorvastatin of 40 mg or more), beta blockers, calcium blockers and ACE inhibitors.

Results

Study Population: Between August 2008 and May 2010, 901 patients with stable coronary disease attending for routine out-patient cardiology review were assessed for eligibility for the study. Of these, 297 [33%] did not meet the entry criteria, 72 [8%] declined to participate and 532 [59%] were enrolled into the study, 250 of whom were randomized to the control group and 282 to treatment. Of those randomized to treatment 32 [11%] reported early intolerance, due to gastrointestinal side effects, and 7 patients subsequently reported that they chose not start therapy (FIG. 1). All 532 randomized patients were followed for the duration of the study period which ranged from a minimum of 24 to a maximum of 44 months. Median follow up was 36 months.

Baseline characteristics according to 'randomized treatment groups are shown in Table. 1. Both groups were well matched for important clinical characteristics although more patients in the colchicine group were taking calcium channel blockers and less were taking beta-blocker therapy. Almost all patients in each group were taking anti-platelet therapy and high dose statin therapy.

TABLE 1

Study Population

| | Control n [%] | Treatment n [%] |
|---|---|---|
| Total | 250 | 282 |
| Mean Age | 67 ± 9.2 | 66 ± 9.6 |
| Males | 222 [89] | 251 [89] |
| Diabetic | 69 [28] | 92 [33] |
| Smoker | 14 [6] | 10 [4] |
| Past AMI or UA | 61 [24] | 64 [23] |
| CABG | 39 [16] | 62 [22] |
| PTCA | 138 [55] | 169 [60] |
| Aspirin and/or Plavix | 235 [94] | 262 [93] |
| DAPT | 24 [10] | 38 [13] |
| High Dose Statins | 235 [94] | 271 [96] |
| BB[1] | 178 [71] | 176 [62] |
| CBB[2] | 25 [10] | 52 [18] |
| ACE | 150 [60] | 155 [55] |

[1] $p < 0.05$
[2] $p < 0.01$ for the comparison of the distributions between treatment and control Past AMI or UA History of myocardial infarction or unstable angina
CABG Coronary Artery Bypass Surgery
PTCA History of Percutaneous Coronary Angioplasty
DAPT Dual anti-platelet therapy [Aspirin and Clopidogrel]
BB Beta-blocker therapy,
CCB Calcium Chanel Blocker therapy
ACE ACE inhibitor therapy Late discontinuations: 30 patients ceased colchicine therapy after a mean period of 2.36 years. Therapy was ceased due to an unrelated inter-current illness in 11 patients, by choice in 5, and for a variety of possible drug related effects in 14 patients [4.9%] as described in Table 2.

TABLE 2

Withdrawals from therapy

| | n [ %] |
|---|---|
| Early Withdrawals | 32 [11] |
| Late Withdrawals* | 30 [11] |
| Unrelated inter-current illness | 11 [3.9] |
| Patient Choice | 5 [1.8] |
| Perceived Side effects | |
| Intestinal upset | 7 [2.5] |
| Myalgia | 2 [0.90] |
| Myositis | 1 [<0.5] |
| Rash | 1 [<0.5] |
| Alopecia | 1 [<0.5] |
| Itch | 1 [<0.5] |
| Peripheral Neuritis | 1 [<0.5] |

*Withdrawals after 30 days, Average time to withdrawal 2.36 years

Outcomes; A primary outcome occurred in 55/532 patients, including 15/282 [5.3%] patients assigned to colchicine treatment, and 40/250 [16%] patients assigned to the control group [hazard ratio 0.33, 95% CI; 0.18-0.59; p<0.001, number needed to treat 11]. A sensitivity analysis was performed for the primary outcome, adjusting for the usage of calcium channel blockers and beta blocker therapy. These results were consistent with the primary analysis.

Figure 2:
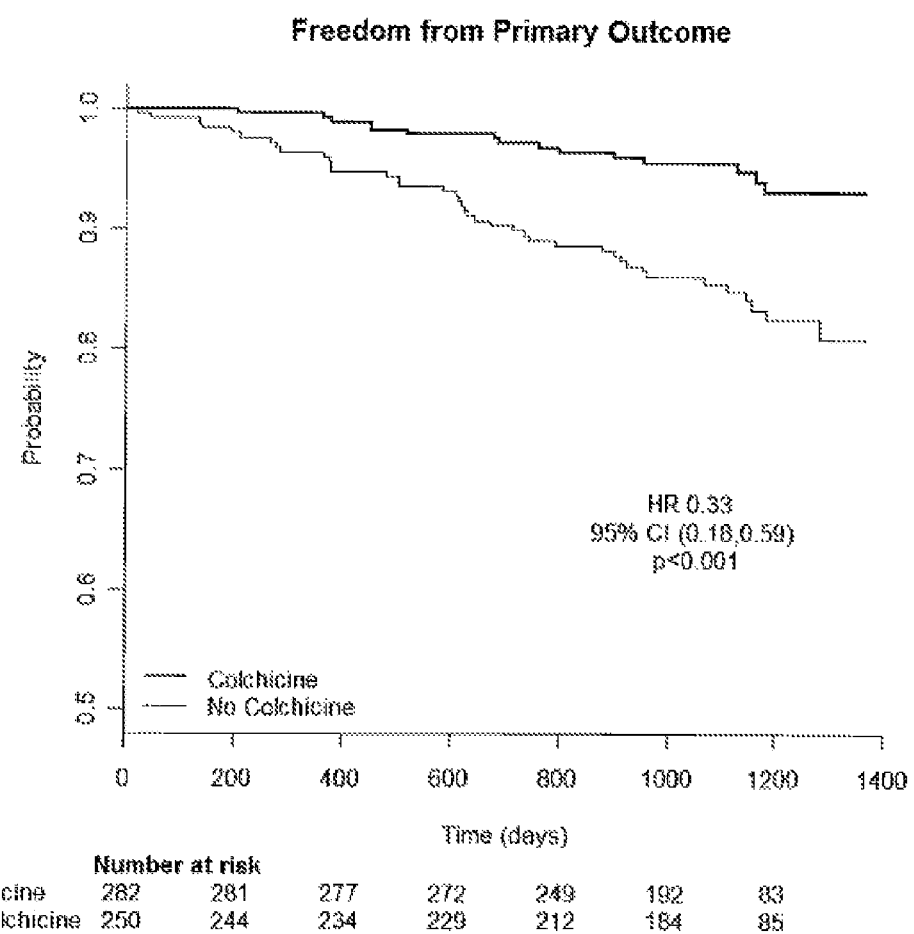
FIG. 2 is a graph of the time to first clinical event in each group by treatment.
Figure 3:
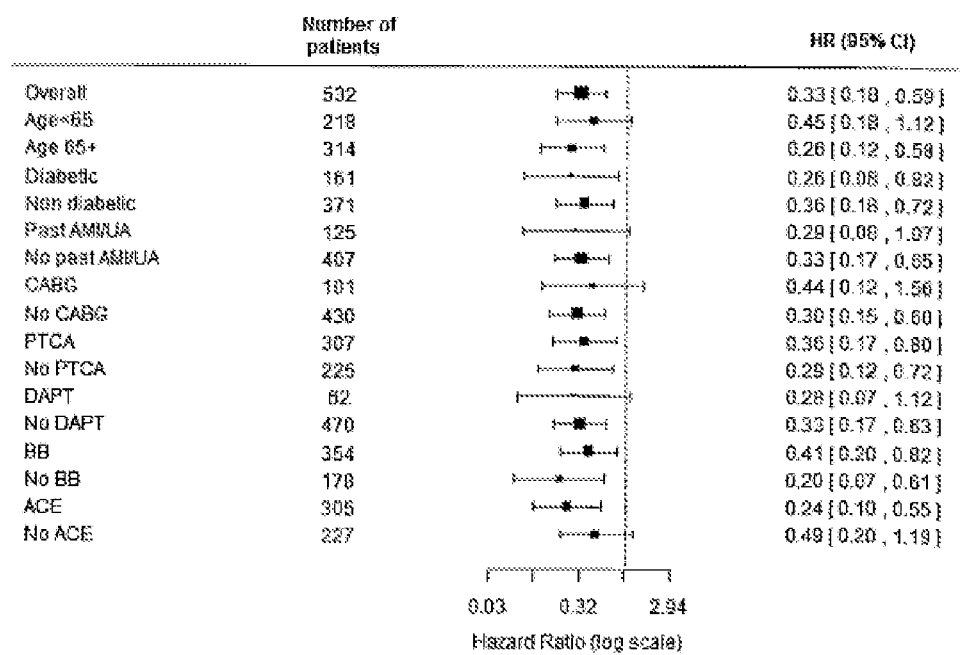
FIG. 3 is a table of the first time to clinical event across subgroups examined.

The time to first clinical event in each group by treatment is shown in FIG. 2. The effect of colchicine on the primary outcome was evident early and the benefits of colchicine continued to accrue throughout the follow up period. Results of the primary analysis were consistent in all subgroups examined (FIG. 3); There was no evidence of differential treatment effects based on any of the clinical or therapeutic variables.

Figure 4:
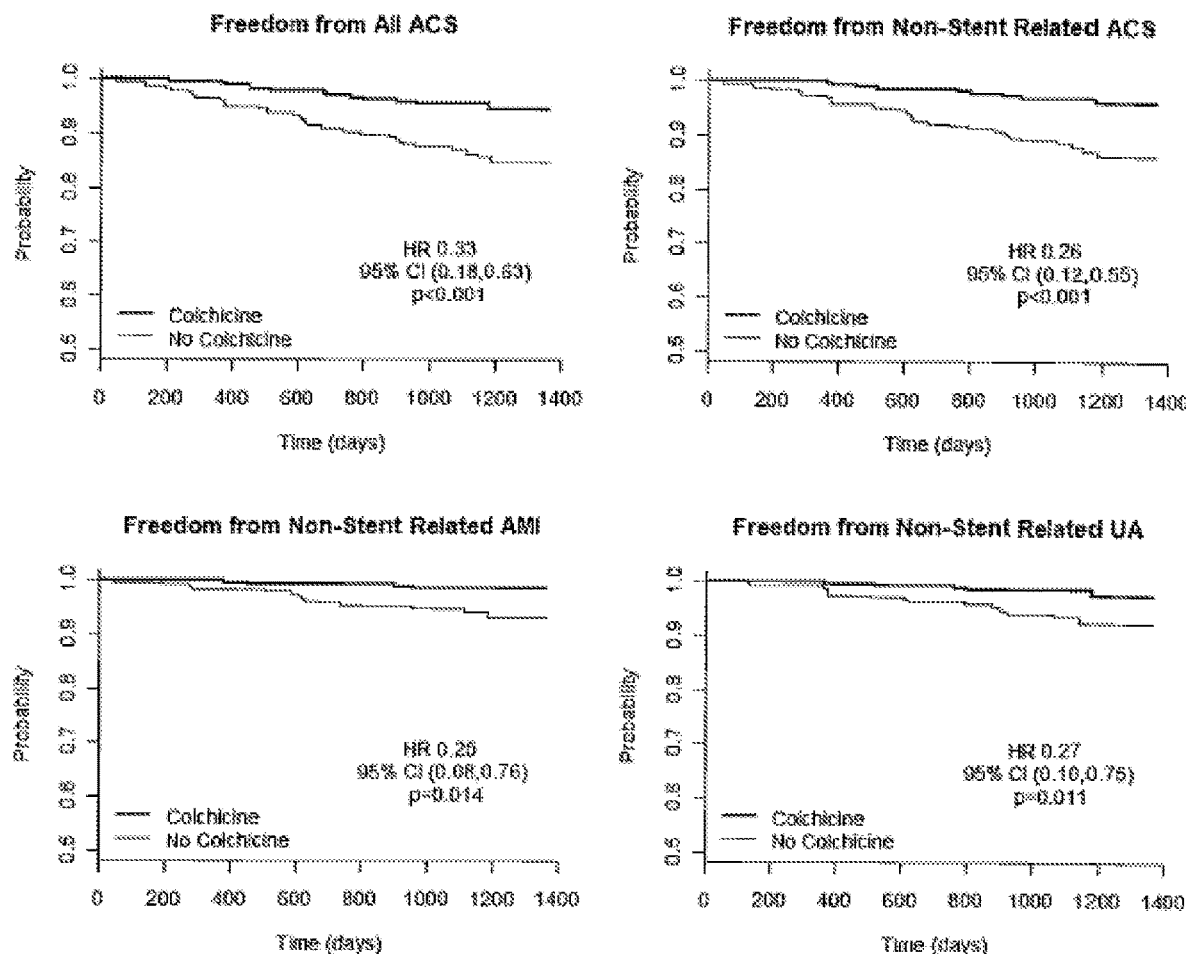
FIG. 4 is series of graphs of the time to first clinical event in each group by treatment broken down into specific events.

The reduction in the primary outcome was largely driven by the reduction in the number of patients presenting with an ACS, [13/282 [4.6%] vs 34/250 [13.4%], hazard ratio 0.33; 95% CI; 0.18-0.63; p<0.001]. Out of hospital cardiac arrest and non-cardio-embolic ischemic stroke were infrequent but were also reduced in the treatment group (Table 3).

that patients randomized to treatment were less likely to present with an ACS unrelated to stent disease (9/282 [3.2%] vs 30/250 [12%] hazard ratio 0.26, 95% CI; 0.12-0.55; p<0.001), be it associated with an AMI (4/282 [1.4%] vs 14/250 [5.6%] hazard ratio 0.25, 95% CI; 0.08-0.76; p=0.014) or UA (5/282 [1.8%] vs 16/250 [6.4%] hazard ratio 0.27, 95% CI; 0.10-0.75; p=0.011). (FIG. 4, Table 3)

Of 39 patients randomized to treatment who did not receive therapy beyond the first month due to early intolerance or non-compliance, 4 [10%] presented with an ACS due to acute stent thrombosis (n=1) and UA (n=3). Patients who were both compliant and tolerant to therapy beyond the first month of randomization had significantly fewer events

TABLE 3

Primary Outcome and its Components

| | Control [n = 250] n [%] | Treatment [n = 282] n [%] | HR 95% CI | p value |
|---|---|---|---|---|
| Primary Outcome | 40 [16] | 15 [5.3] | 0.33; 0.18-0.59 | <0.001 |
| Components of Primary Outcome | | | | |
| Acute Coronary Syndrome | 34 [13.6] | 13 [4.6] | 0.33; 0.18-0.63 | <0.001 |
| OOH Cardiac Arrest | 2 [0.8] | 1 [0.35][1] | 0.47; 0.04-5.15 | 0.534 |
| Non-Cardio-Embolic Stroke | 4 [1.6] | 1 [0.35] | 0.23; 0.03-2.03 | 0.184 |
| Components of ACS | | | | |
| Stent Related | 4 [1.6] | 4 [1.4] | NS | |
| Non-Stent Related | 30 [12] | 9 [3.2] | 0.26; 0.12-0.55 | <0.001 |
| Non-Stent Related AMI | 14 [5.6] | 4 [1.6] | 0.25; 0.08-0.76 | 0.014 |
| Non-Stent Related UA | 16 [12] | 5 [2.4] | 0.27; 0.10-0.75 | 0.011 |

OOH Out of Hospital
ACS Acute Coronary Syndrome
AMI Acute Myocardial Infarction
UA Unstable Angina
[1]Non-Fatal Of the 47 patients who presented with an ACS, the event was stent related in 8 [17%] [2 in each group had evidence of acute stent thrombosis and 2 in each group had evidence of significant in-stent stenosis]. Further analysis confirmed than the control patients (11/243 [4.5%] vs 40/250 [16%] hazard ratio 0.29, 95% CI; 0.15-0.56; p<0.001). The results of all on-treatment analyses were consistent with those based upon the intention to treat analyses (Table 4).

TABLE 4

Primary Outcome and its Components [On-Treatment Analysis]

| | Control [n = 250] n [%] | Treatment [n = 243] n [%] | HR; 95% CI | p-value |
|---|---|---|---|---|
| Primary Outcome | 40 [16] | 11 [5.3] | 0.29 .(0.15, 0.56) | <0.001 |
| Components of Primary Outcome | | | | |
| Acute Coronary Syndrome | 34 [13.6] | 9 [4.6] | 0.28 (0.13, 0.58) | <0.001 |
| OOH Cardiac Arrest | 2 [0.8] | 1 [0.35][1] | 0.55 (0.05, 6.03) | 0.622 |
| Non-Cardio-Embolic Stroke | 4 [1.6] | 1 [0.35] | 0.27 (0.03, 2.42) | 0.242 |
| Components of ACS | | | | |
| Stent Related | 4 [1.6] | 3 [1.4] | NS | |
| Non-Stent Related | 30 [12] | 6 [3.2] | 0.21 (0.09, 0.50) | <0.001 |
| Non-Stent Related AMI | 14 [5.6] | 4 [1.6] | 0.30 (0.10, 0.91) | 0.033 |
| Non-Stent Related UA | 16 [12] | 2 [2.4] | 0.13 (0.03, 0.57) | 0.007 |

OOH Out of Hospital
ACS Acute Coronary Syndrome
AMI Acute Myocardial Infarction
UA Unstable Angina
[1]Non-Fatal Ten patients in the control group died compared with 4 patients in the colchicine group. Of the 10 controls, 5 died of presumed cardiac cause; 2 following an out-of-hospital cardiac arrest, 2 from cardiogenic shock following myocardial infarction, and 1 following bypass surgery. All 4 patients in the colchicine group died of non-cardiac causes.

The LoDoCo trial demonstrates that the addition of colchicine 0.5 mg/day to standard therapy in patients with stable coronary disease significantly reduces the risk of a cardiovascular event, including an ACS, out of hospital cardiac arrest and non-cardio-embolic ischemic stroke. The benefits of colchicine were achieved on a background of widespread use of effective secondary prevention strategies, including high dose statins, as evidenced by the low event rate in the control group. The effect of adding colchicine became evident early, continued to accrue over time and was largely driven by a reduction in ACS unrelated to stent disease.

Numerous variations and modifications will suggest themselves to persons skilled in the relevant art, in addition to those already described, without departing from the basic inventive concepts. All such variations and modifications are to be considered within the scope of the present invention, the nature of which is to be determined from the foregoing description.

The invention claimed is:

1. A method for reducing a risk of at least one cardiovascular event in a subject in need thereof, which comprises:
   administering, orally once per day to the subject, a composition comprising about 0.5 total mg of (i) colchicine, (ii) a pharmaceutically acceptable salt of (i), or any combination of (i) and (ii),
   wherein the at least one cardiovascular event is chosen from myocardial infarction (MI), stroke, coronary revascularization, unstable angina requiring hospitalization, cardiac arrest, and cardiovascular death;
   wherein the subject has no contra-indications to colchicine therapy, and has at least one risk factor chosen from:
   i. an age greater than or equal to 35;
   ii. diabetes;
   iii. past myocardial infarction;
   iv. unstable angina;
   v. coronary bypass surgery;
   vi. coronary angioplasty; and
   vii. therapy with at least one drug chosen from aspirin, clopidogrel, statins, beta blockers, calcium blockers, and ACE inhibitors; and
   wherein the composition reduces the risk of the subject experiencing the at least one cardiovascular event by a greater percentage than a composition that does not include colchicine or the pharmaceutically acceptable salt thereof.

2. The method of claim 1, wherein the composition is in a form of a tablet or a capsule.

3. The method of claim 1, wherein the composition is in a form of a liquid dose, a gel, or a powder.

4. The method of claim 1, wherein the risk of the at least one cardiovascular event is reduced by at least about 10% compared to a composition that does not include colchicine or a pharmaceutically acceptable salt thereof.

5. The method of claim 1, wherein the risk of the at least one cardiovascular event is reduced by at least about 20% compared to a composition that does not include colchicine or a pharmaceutically acceptable salt thereof.

6. The method of claim 1, wherein the risk of the at least one cardiovascular event is reduced by at least about 30% compared to a composition that does not include colchicine or a pharmaceutically acceptable salt thereof.

7. The method of claim 1, wherein the risk of the at least one cardiovascular event is reduced by at least about 40% compared to a composition that does not include colchicine or a pharmaceutically acceptable salt thereof.

8. The method of claim 1, wherein the risk of the at least one cardiovascular event is reduced by at least about 50% compared to a composition that does not include colchicine or a pharmaceutically acceptable salt thereof.

9. The method of claim 1, wherein the contra-indications to colchicine therapy is chronic kidney disease.

10. The method of claim 1, wherein the subject is from about 35 to about 85 years of age.

11. The method of claim 1, wherein the at least one cardiovascular event is MI.

12. The method of claim 1, wherein the at least one cardiovascular event is stroke.

13. The method of claim 1, wherein the at least one cardiovascular event is coronary revascularization.

14. The method of claim 1, wherein the at least one cardiovascular event is unstable angina requiring hospitalization.

15. The method of claim 1, wherein the at least one cardiovascular event is cardiac arrest.

16. The method of claim 1, wherein the at least one cardiovascular event is cardiovascular death.

17. The method of claim 1, wherein the subject is administered the composition daily for at least 24 months.

18. The method of claim 1, wherein the subject is administered the composition daily for at least 36 months.

19. The method of claim 1, wherein the subject is administered the composition daily for at least 44 months.

20. The method of claim 1, further comprising co-administering to the subject a therapeutically effective amount of a second agent for reducing the risk of the at least one cardiovascular.

21. The method of claim 17, wherein the second agent is a colchicine-compatible statin.

22. The method of claim 18, wherein the statin is chosen from atorvastatin, fluvastatin, lovastatin, pitavastatin, rosuvastatin, simvastatin, pravastatin, a salt thereof, and any combination thereof.

23. A method for reducing a risk of at least one cardiovascular event in a subject in need thereof, which comprises:
   administering, orally once per day to the subject, a composition comprising about 0.5 total mg of (i) colchicine, (ii) a pharmaceutically acceptable salt of (i), or any combination of (i) and (ii), and
   co-administering to the subject a therapeutically effective amount of a second agent;
   wherein the at least one cardiovascular event is chosen from myocardial infarction (MI), stroke, coronary revascularization, unstable angina requiring hospitalization, cardiac arrest, and cardiovascular death;
   wherein the subject has no contra-indications to colchicine therapy, and has at least one risk factor chosen from:
   i. an age greater than or equal to 35;
   ii. diabetes;
   iii. past myocardial infarction;
   iv. unstable angina;
   v. coronary bypass surgery;
   vi. coronary angioplasty; and
   vii. therapy with at least one drug chosen from aspirin, clopidogrel, statins, beta blockers, calcium blockers, and ACE inhibitors; and wherein the composition reduces the risk of the subject experiencing the at least one cardiovascular event by a greater percentage than a composition that does not include colchicine or a pharmaceutically acceptable salt thereof.

24. A method for reducing a risk of at least one cardiovascular event in a subject in need thereof, which comprises:
administering, orally once per day to the subject, a composition comprising about 0.5 total mg of (i) colchicine, (ii) a pharmaceutically acceptable salt of (i), or any combination of (i) and (ii), and
continuing orally administering to the subject the composition once per day for a duration ranging from 24 months to 44 months;
wherein the at least one cardiovascular event is chosen from myocardial infarction (MI), stroke, coronary revascularization, unstable angina requiring hospitalization, cardiac arrest, and cardiovascular death;
wherein the subject has no contra-indications to colchicine therapy, and has at least one risk factor chosen from:
i. an age greater than or equal to 35;
ii. diabetes;
iii. past myocardial infarction;
iv. unstable angina;
v. coronary bypass surgery;
vi. coronary angioplasty; and
vii. therapy with at least one drug chosen from aspirin, clopidogrel, statins, beta blockers, calcium blockers, and ACE inhibitors; and
wherein the composition reduces the risk of the subject experiencing the at least one cardiovascular event by a greater percentage than a composition that does not include colchicine or a pharmaceutically acceptable salt thereof.

* * * * *